United States Patent
Hermans et al.

(10) Patent No.: US 10,130,935 B2
(45) Date of Patent: Nov. 20, 2018

(54) ENHANCED DISPERSION OF TWO-DIMENSIONAL METAL OXIDE SURFACE SPECIES ON SILICA USING AN ALKALI PROMOTER

(71) Applicant: Wisconsin Alumni Research Foundation, Madison, WI (US)

(72) Inventors: Ive Hermans, Madison, WI (US); Joseph Thomas Grant, Madison, WI (US); Carlos Carrero Marquez, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 50 days.

(21) Appl. No.: 15/016,850

(22) Filed: Feb. 5, 2016

(65) Prior Publication Data

US 2016/0228851 A1    Aug. 11, 2016

Related U.S. Application Data

(60) Provisional application No. 62/112,689, filed on Feb. 6, 2015.

(51) Int. Cl.
   *B01J 23/20* (2006.01)
   *B01J 23/22* (2006.01)
   (Continued)

(52) U.S. Cl.
   CPC ............... *B01J 23/22* (2013.01); *B01J 21/08* (2013.01); *B01J 23/20* (2013.01); *B01J 23/28* (2013.01);
   (Continued)

(58) Field of Classification Search
   None
   See application file for complete search history.

(56) References Cited

U.S. PATENT DOCUMENTS

| 2,504,001 A | 4/1950 | Connolly |
| 3,207,703 A | 9/1965 | Innes |

(Continued)

FOREIGN PATENT DOCUMENTS

| GB | 2277887 | 11/1994 |

OTHER PUBLICATIONS

La Parola, V., et al., "Structural characterisation of silica supported CoMo catalysts by UV Raman spectroscopy, XPS and X-ray diffraction techniques," Applied Catalysis A: General, Elsevier Science, Amsterdam, NL, vol. 235, No. 1-2, Aug. 30, 2002, pp. 171-180.

(Continued)

*Primary Examiner* — Colin W. Slifka
(74) *Attorney, Agent, or Firm* — Boyle Fredrickson S.C.

(57) ABSTRACT

Improved catalysts including two-dimensional metal oxide species highly dispersed on a silica support are disclosed, as well methods of making and using such catalysts. The catalysts are substantially free of metal oxide nanoparticles. The higher than expected maximum dispersion densities are obtained in the catalysts by introducing dispersion-promoting sodium ions, and optionally, aluminum ions, onto the silica support. The improved catalysts may be used in a variety of chemical processes, including, without limitation, in dehydrogenation, oxidation, and metathesis reactions.

18 Claims, 33 Drawing Sheets

(51) Int. Cl.
- *B01J 23/28* (2006.01)
- *B01J 23/30* (2006.01)
- *B01J 37/02* (2006.01)
- *C07C 45/52* (2006.01)
- *C07C 5/48* (2006.01)
- *B01J 21/08* (2006.01)
- *C07C 6/04* (2006.01)
- *B01J 35/00* (2006.01)
- *B01J 35/10* (2006.01)
- *B01J 37/08* (2006.01)
- *B01J 29/03* (2006.01)

(52) U.S. Cl.
CPC ............ *B01J 23/30* (2013.01); *B01J 35/002* (2013.01); *B01J 35/0066* (2013.01); *B01J 35/10* (2013.01); *B01J 37/0203* (2013.01); *B01J 37/0207* (2013.01); *B01J 37/0215* (2013.01); *C07C 5/48* (2013.01); *C07C 6/04* (2013.01); *C07C 45/52* (2013.01); *B01J 29/0341* (2013.01); *B01J 35/1019* (2013.01); *B01J 37/082* (2013.01); *B01J 2523/00* (2013.01); *C07C 2521/04* (2013.01); *C07C 2521/06* (2013.01); *C07C 2523/20* (2013.01); *C07C 2523/22* (2013.01); *C07C 2523/26* (2013.01); *C07C 2523/28* (2013.01); *C07C 2523/30* (2013.01); *C07C 2523/36* (2013.01); *Y02P 20/52* (2015.11)

(56) References Cited

U.S. PATENT DOCUMENTS

| | | |
|---|---|---|
| 3,249,558 A | 5/1966 | Kearby |
| 6,544,924 B1 | 4/2003 | Jackson |
| 7,399,457 B2 | 7/2008 | Cross et al. |
| 2005/0205465 A1 | 9/2005 | Peters |
| 2007/0265360 A1 | 11/2007 | Luo |
| 2009/0308792 A1* | 12/2009 | Wu ................. B01J 31/04 208/216 R |

OTHER PUBLICATIONS

International Search Report and Written Opinion, dated Sep. 7, 2016, International Patent Application No. PCT/US2016/016772.

Joseph T. Grant, Carlos A. Carrero, Alyssa M. Love, Rene Verel, and Ive Hermans, Enhanced Two-Dimensional Dispersion of Group V Metal Oxides on Silica, ACS Catalysis, Oct. 2, 2015, pp. 5787-5793, vol. 5, Issue 10, ACS Publications, Washington D.C.

* cited by examiner

ENHANCED DISPERSION OF TWO-DIMENSIONAL METAL OXIDE SURFACE SPECIES ON SILICA USING AN ALKALI PROMOTER

CROSS REFERENCE TO RELATED APPLICATIONS

This application claims the benefit of U.S. Provisional Patent Application Ser. No. 62/112,689, filed Feb. 6, 2015, which is incorporated by reference herein as if set forth in its entirety.

STATEMENT REGARDING FEDERALLY SPONSORED RESEARCH OR DEVELOPMENT

N/A

FIELD OF THE INVENTION

The disclosure relates generally to metal oxide catalysts that are highly dispersed in a two-dimensional form on a silica support, as well as methods of making and using such catalysts.

BACKGROUND OF THE INVENTION

Supported metal oxides are an important class of heterogeneous catalysts for a variety of chemical applications, including for use in biodiesel production, destructive adsorption of chlorocarbons and chemical warfare agents, and in natural gas upgrading processes such as alkane oxidation, olefin metathesis, and oxidative propane dehydrogenation (ODHP; see FIG. 1).

Structurally, supported metal oxides include one or more metal oxide species loaded onto the surface of an inert support material, whereby the metal oxide species is bonded to the support material. Silica ($SiO_2$), given its abundance and low cost, has traditionally been an important inert support material for such catalysts. Examples of commonly used metal oxides include group 3 metal oxides, such as aluminium oxide; group 4 metal oxides, such as titanium oxide; group 5 metal oxides, such as vanadium oxide, niobium oxide, and tantalum oxide; group 6 metal oxides, such as chromium oxide, molybdenum oxide, and tungsten oxide; and group 7 metal oxides, such as rhenium oxide.

At low metal oxide loadings (i.e, at loading levels insufficient to form a complete metal oxide monolayer on the support surface), the metal oxide species bonded to the support material surface are two-dimensional (typically monomeric, but in some case, oligomeric) species that are dispersed throughout the support material surface. As illustrated in FIG. 2, group 5 metal oxide monomers form monoxo structures, group 6 metal oxide monomers form dioxo structures, and group 7 metal oxide monomers form trioxo structures. Each of these structures exhibits tetrahedral geometry around the central metal atom when supported on silica, although the tetrahedron is somewhat distorted in the group 6 and group 7 monomers.

At sub-monolayer loadings, increased metal oxide loading generally results in increased dispersion (i.e., greater surface density) of the metal within the metal oxide catalyst. This increased dispersion generally increases the efficiency of the catalyst, because more catalytic sites are present within a given surface area of the support. However, at higher loading levels, metal oxide species in the form of three-dimensional nanoparticles begin to form on the support surface. As shown in FIG. 3, such nanoparticles exhibit non-tetrahedral geometry around the central metal atoms. The presence of such nanoparticles can be detrimental to the activity of the catalyst, because the presence of nanoparticles increases the rate of side reactions that compete with the desired reaction, thus reducing the yield and efficiency of production of the desired product.

For example, referring now to FIG. 1, which illustrates the production of propylene by oxidative propane dehydrogenation (ODHP), $k_1$ shows the desired production of propylene from propane, while k2 and k3 show the combustion of reactant and product, respectively, to form $CO_x$, a competing side reaction that decreases the efficiency of production of the desired product. The presence of metal oxide nanoparticles on the support surface detrimentally increases the rate of these combustion side reactions. Thus, ideally, metal oxide catalysts are deposited onto the support at a level low enough such that the support surface remains substantially free of metal oxide nanoparticles, yet still at a level high enough to maximize surface density of the monomeric metal oxide species.

Metal oxides on silica, however, have only been able to form dispersed species without nanoparticle formation at very low metal loadings, as compared to other commonly used support materials. Specifically, the highest reported value for dispersion of vanadium on silica is only about 3 vanadium-atoms/$nm^2$, while on other support materials (e.g., $Al_2O_3$, $TiO_2$, and $ZrO_2$), dispersed vanadium can exist at surface densities as high as 9 vanadium-atoms/$nm^2$. Similarly, the highest reported value for dispersion of niobium on silica is only 1.1 niobium-atoms/$nm^2$, and the highest reported value for dispersion of tantalum on silica is only 0.8 tantalum-atoms/$nm^2$. These relatively low maximum dispersion densities using silica as a catalytic support have been attributed to the low reactivity of the surface hydroxyls of silica.

Accordingly, there is a need in the art for methods of increasing the low maximum dispersion thresholds for metal oxide catalysts supported on silica surfaces, and for substantially nanoparticle-free catalysts comprising highly dispersed metal oxides on silica supports.

BRIEF SUMMARY

As a result of the surprising discovery that sodium ion in low concentrations can be used to enhance dispersion of metal oxide catalysts on silica support surfaces, the inventors have developed improved metal oxide catalysts for use in a variety of processes, as well as methods of producing and using such catalysts.

Accordingly, in a first aspect, the disclosure encompasses a heterogeneous catalyst that includes one or more two-dimensional metal oxide species highly dispersed on the surface of a silica support that further comprises ions of one or more alkali metals, wherein the metal oxide is an oxide of a group 3, group 4, group 5, group 6 or group 7 metal, and wherein the catalyst is substantially free of metal oxide nanoparticles.

By "highly dispersed," we mean that the one or more two-dimensional metal oxide species occur on the surface of the silica support at a dispersion density that is higher than the maximum dispersion density previously known for a specific metal oxide on the surface of a silica support. By "substantially free of nanoparticles," we mean that any nanoparticles present are not detectable using conventional means of detection, including by Raman spectroscopy or UV-vis spectroscopy.

The enhanced dispersion of 2D metal oxides via sodium promotion is not exclusive to amorphous silica, but also includes application to mesoporous silica. Mesoporous silica is crystalline in structure and contains ordered pore structure. Exemplary mesoporous silica for use in the invention include SBA-15 and MCM-41 types.

In some embodiments, the mole ratio of the alkali metal ions present to the metal atoms of the metal oxide present is less than 0.25/1.

In some embodiments, the one or more two-dimensional metal oxide species are monomeric species.

In some embodiments, the one or more two-dimensional metal oxide species exhibit tetrahedral geometry around the metal atoms.

In some embodiments, the metal oxide is an oxide of a group 5, group 6 or group 7 metal. In some such embodiments, the metal oxide is an oxide of a group 5 or group 6 metal. In some such embodiments, the metal oxide is an oxide of a group 5 metal.

In some embodiments, the metal oxide is vanadium oxide, niobium oxide, tantalum oxide, chromium oxide, molybdenum oxide, tungsten oxide, rhenium oxide, titanium oxide, or mixtures thereof. In some such embodiments, the metal oxide is vanadium oxide, niobium oxide, tantalum oxide, titanium oxide; or mixtures thereof. If vanadium oxide is the metal oxide, it may optionally be dispersed on the surface of the silica support in the range of 3.2-10 V-atoms/nm$^2$; 3.5-10 V-atoms/nm$^2$; 4-10 V-atoms/nm$^2$; 5-10 V-atoms/nm$^2$; 6-10 V-atoms/nm$^2$; 3.2-9 V-atoms/nm$^2$; 3.5-9 V-atoms/nm$^2$; 4-9 V-atoms/nm$^2$; 5-9 V-atoms/nm$^2$; or 6-9 V-atoms/nm$^2$. If niobium oxide is selected, it may optionally be dispersed on the surface of the silica support in the range of 1.2-6 Nb-atoms/nm$^2$; 1.5-6 Nb-atoms/nm$^2$; 2-6 Nb-atoms/nm$^2$; 1.2-5 Nb-atoms/nm$^2$; 1.5-5 Nb-atoms/nm$^2$; 2-5 Nb-atoms/nm$^2$; 1.2-4 Nb-atoms/nm$^2$; 1.5-4 Nb-atoms/nm$^2$; 2-4 Nb-atoms/nm$^2$; 1.2-3 Nb-atoms/nm$^2$; 1.5-3 Nb-atoms/nm$^2$; or 2-4 Nb-atoms/nm$^2$. If tantalum oxide is selected, it may optionally be dispersed on the surface of the silica support in the range of 1-6 Ta-atoms/nm$^2$; 1-5 Ta-atoms/nm$^2$; 2-6 Ta-atoms/nm$^2$; or 2-5 Ta-atoms/nm$^2$.

In some embodiments, the ions of one or more alkali metals are sodium ions. In certain embodiments, the sodium ions are present in the silica support at a concentration of about 0.15-1.4 Na-ions/nm$^2$, preferably 0.3-1.0 Na-ions/nm$^2$, more preferably 0.4-0.8 Na-ions/nm$^2$, or, most preferably, about 0.6 Na-ions/nm$^2$.

In some embodiments, the silica support further comprises aluminum ions. In some such embodiments, the aluminum ions are optionally present in the silica support at a concentration of less than 1000 ppm. In some embodiments, the silica support does not comprise aluminum ions.

In a second aspect, the disclosure encompasses a method of making a desired chemical product. The method includes the step of contacting a liquid or gaseous reactant with the heterogeneous catalyst as described above, whereby the desired chemical product is formed by a process catalyzed by the heterogeneous catalyst.

In some embodiments, the liquid or gaseous reactant is an alkane, the process catalyzed by the heterogeneous catalyst is oxidative dehydrogenation, and the desired chemical product is an olefin. In some such embodiments, the metal oxide in the heterogeneous catalyst is selected from the group consisting of vanadium oxide, chromium oxide, molybdenum oxide, aluminum oxide, tantalum oxide, nobium oxide, titanium oxide, rhenium oxide, and mixtures thereof. In certain preferred embodiments, the metal oxide in the heterogeneous catalyst is vanadium oxide.

In some embodiments, the liquid or gaseous reactant is an alkane, the process catalyzed by the heterogeneous catalyst is non-oxidative dehydrogenation, and the desired chemical product is an olefin. In some such embodiments, the metal oxide in the heterogeneous catalyst is selected from the group consisting of vanadium oxide, chromium oxide, molybdenum oxide, aluminum oxide, tantalum oxide, nobium oxide, titanium oxide, rhenium oxide, and mixtures thereof. In certain embodiments, the metal oxide in the heterogeneous catalyst is chromium oxide, molybdenum oxide, vanadium oxide, or mixtures thereof.

In some embodiments, the liquid or gaseous reactant is an alkane, the process catalyzed by the heterogeneous catalyst is alkane oxidation, and the desired chemical product is an oxygenate. In some such embodiments, the metal oxide in the heterogeneous catalyst is selected from the group consisting of vanadium oxide, chromium oxide, molybdenum oxide, aluminum oxide, tantalum oxide, nobium oxide, titanium oxide, rhenium oxide, and mixtures thereof. In certain preferred embodiments, the metal oxide in the heterogeneous catalyst is molybdenum oxide.

In some embodiments, the liquid or gaseous reactant comprises one or more olefins, the process catalyzed by the heterogeneous catalyst is olefin metathesis, and the desired chemical product comprises one or more olefins that are different than the olefins of which the liquid or gaseous reactant is comprised. In some such embodiments, the metal oxide in the heterogeneous catalyst is selected from the group consisting of vanadium oxide, chromium oxide, molybdenum oxide, aluminum oxide, tantalum oxide, nobium oxide, titanium oxide, rhenium oxide, and mixtures thereof. In certain preferred embodiments, the metal oxide in the heterogeneous catalyst is tungsten oxide, molybdenum oxide, rhenium oxide, or mixtures thereof.

In some embodiments, the liquid or gaseous reactant is a chlorocarbon, the process catalyzed by the heterogeneous catalyst is chlorocarbon degradation, and the desired chemical product comprise products of chlorocarbon degradation. In some such embodiments, the metal oxide in the heterogeneous catalyst is selected from the group consisting of vanadium oxide, chromium oxide, molybdenum oxide, aluminum oxide, tantalum oxide, nobium oxide, titanium oxide, rhenium oxide, and mixtures thereof. In certain preferred embodiments, the metal oxide in the heterogeneous catalyst is niobium oxide.

In some embodiments, the liquid or gaseous reactant is glycerol, the process catalyzed by the heterogeneous catalyst is glycerol conversion, and the desired chemical product is acrolein. In some such embodiments, the metal oxide in the heterogeneous catalyst is selected from the group consisting of vanadium oxide, chromium oxide, molybdenum oxide, aluminum oxide, tantalum oxide, nobium oxide, titanium oxide, rhenium oxide, and mixtures thereof. In certain preferred embodiments, the metal oxide is niobium oxide, tungsten oxide, or mixtures thereof.

In a third aspect, the disclosure encompasses a method of making a heterogeneous catalyst including one or more two-dimensional metal oxide species highly dispersed on the surface of a silica support. The method includes the steps of (a) contacting a silica support with a solution containing one or more alkali metal ions, resulting in a silica support having an alkali metal promoter; and (b) contacting the silica support having an alkali metal promoter with a composition containing one or more metal oxides or metal oxide precursors, wherein the metal oxide is an oxide of a group 3, group 4, group 5, group 6 or group 7 metal. As a result of performing these steps, one or more two-dimensional metal oxide species are highly dispersed on the surface of the silica support.

In some embodiments, the mole ratio of the alkali metal ions in step (a) to the metal atoms of the metal oxide in step (b) is less than 0.25/1.

In some embodiments, the metal oxide is an oxide of a group 5, group 6 or group 7 metal. In some such embodiments, the metal oxide is an oxide of a group 5 or group 6 metal. In some such embodiments, the metal oxide is an oxide of a group 5 metal.

In some embodiments, the metal oxide is vanadium oxide, niobium oxide, tantalum oxide, chromium oxide, molybdenum oxide, tungsten oxide, rhenium oxide, titanium oxide, or mixtures thereof. In some such embodiments, the metal oxide is vanadium oxide, niobium oxide, tantalum oxide, titanium oxide, or mixtures thereof.

In some embodiments, the one or more alkali metal ions are potassium ions, sodium ions, rubidium ions, or combinations thereof. In some such embodiments, the one or more alkali metal ions are sodium ions. In some embodiments, the ions of one or more alkali metals are sodium ions. In certain embodiments, the sodium ions are present in the silica support at a concentration of about 0.15-1.4 Na-ions/nm$^2$, preferably 0.3-1.0 Na-ions/nm$^2$, more preferably 0.4-0.8 Na-ions/nm$^3$, or, most preferably, about 0.6 Na-ions/nm$^3$.

In some embodiments, the solution containing the one or more alkali metal ions also includes aluminum ions, which results in a silica support having an alkali metal promoter that also includes aluminum ions. In some such embodiments, the aluminum ions are present in the silica support having an alkali metal promoter at a concentration of less than 1000 ppm.

In some embodiments, the solution containing the one or more alkali metal ions does not include aluminum ions.

In some embodiments, either or both of the contacting steps further include calcining the resulting composition.

In some embodiments wherein metal oxide precursors are used, the metal oxide precursors may optionally be one or more metal alkoxides. In some such embodiments, the metal alkoxides are metal isopropoxides.

Further objects, features and advantages of the invention will be apparent from the following detailed description when taken in conjunction with the accompanying drawings.

BRIEF DESCRIPTION OF THE DRAWINGS

The disclosure will be better understood and features, aspects and advantages other than those set forth above will become apparent when consideration is given to the following detailed description thereof. Such detailed description makes reference to the following drawings.

plotted as a function of the vanadium surface coverage. Open symbols (Δ) indicate pro-SiO$_2$ support material, while all others use im-SiO$_2$.

Figure 15:
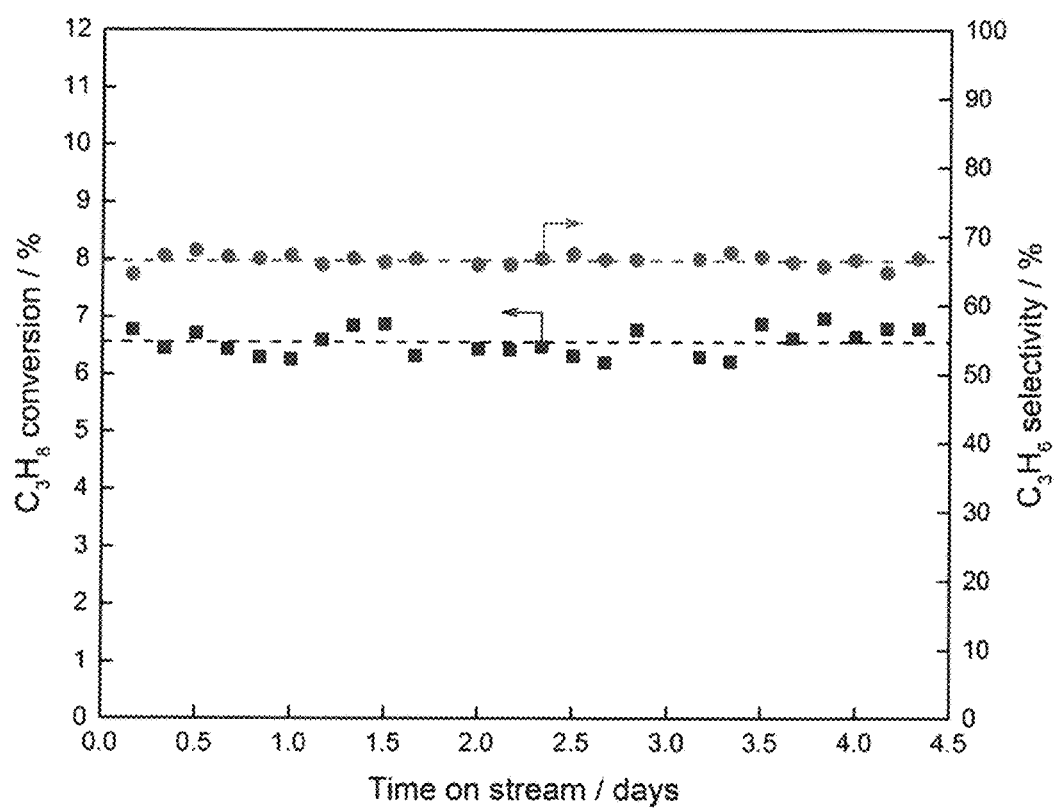

FIG. 15 shows the catalytic activity of 8.6 V nm$^{-2}$ supported on pro-SiO$_2$ for ODHP. Selectivity to propylene remains ~66% with ~6.5% propane conversion for at least 4.5 days on-stream. T=490° C., WHSV$^{-1}$=110 [kg-cat s m$^{-3}$].

Figure 16:
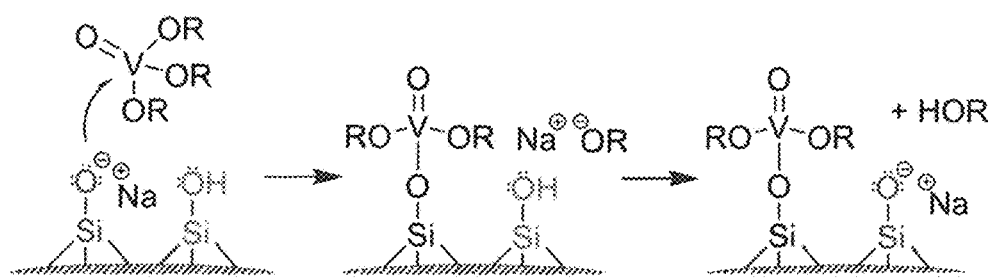

FIG. 16 shows the proposed mechanism for the activation of Silanol Groups by Na$^+$ and the Associated Migration of the Na$^+$ over the Support Surface.

Figure 17:
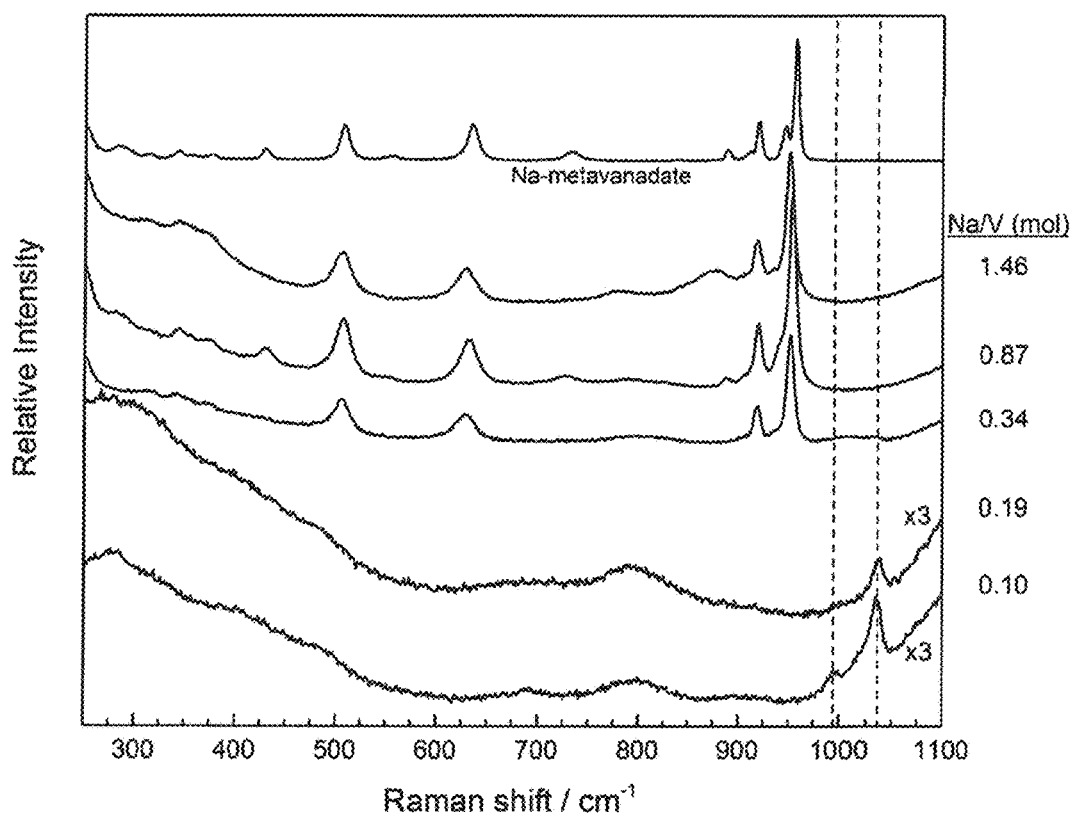

FIG. 17 shows Raman spectra of V/SiO$_2$ catalysts containing varying levels of sodium loadings. Only catalysts containing a Na/V molar ratio ~0.2 shows the enhanced 2D dispersion effect. At lower Na/V ratio, emergence of 3D V$_2$O$_3$ occurs, while higher Na/V ratios shows the formation of Na-metavanadate.

Figure 18:
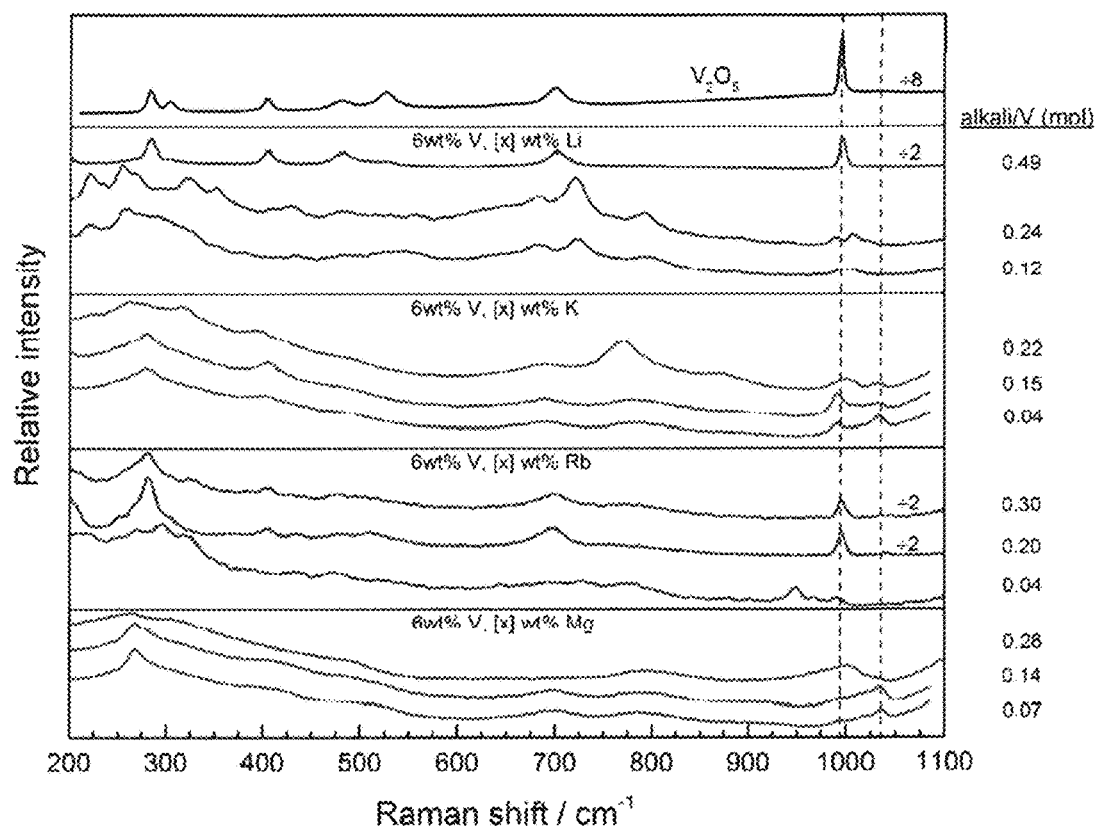

FIG. 18 shows Raman spectra of vanadia supported on varying levels of Li-, K-, Rb-, Mg-promoted SiO$_2$. None of these prepared catalysts show completely 2D vanadia species, contrary to that of vanadia supported on Na-promoted SiO$_2$. Each of the above catalysts show either the emergence of 3D V$_2$O$_5$ bands or unidentified Raman bands, likely due to the formation of a type of Li-, K-, Rb-, or Mg-vanadate material similar to that shown for Na-metavanadate reported here in the text.

Figure 19:
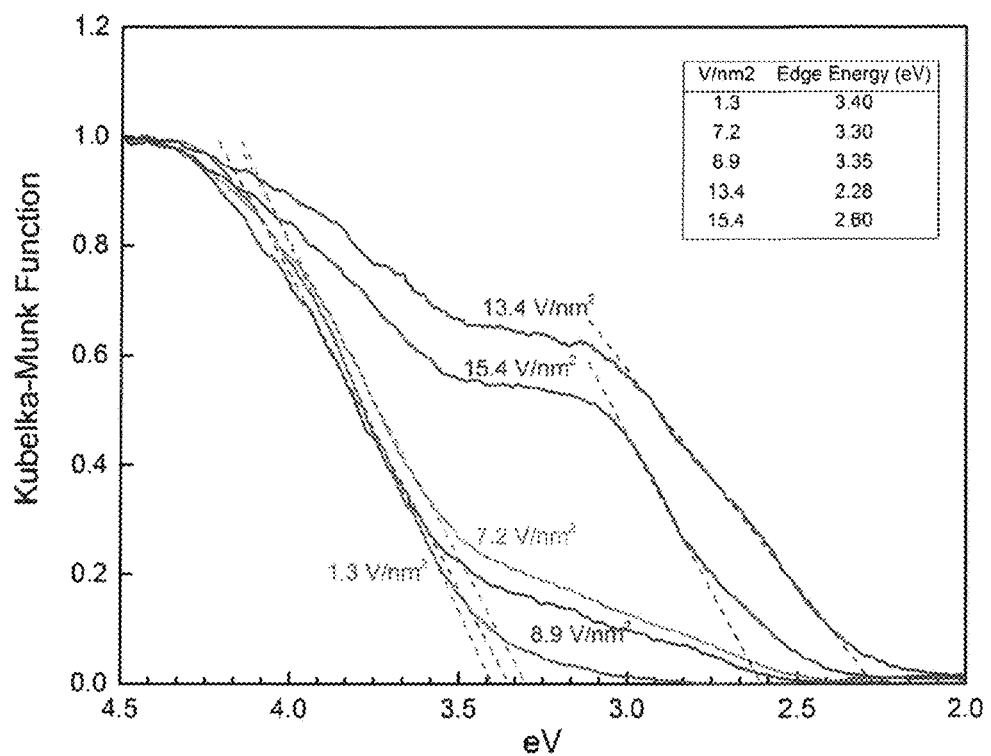

FIG. 19 shows DRUV-vis spectra of dehydrated im-SiO$_2$ catalysts impregnated with varying loadings of vanadia. Only catalysts with highest vanadia surface densities (13.4 and 15.4 V nm$^{-2}$) shift to edge energies of below 3.0 eV, corresponding to 3D V$_2$O$_5$.

Figure 20:
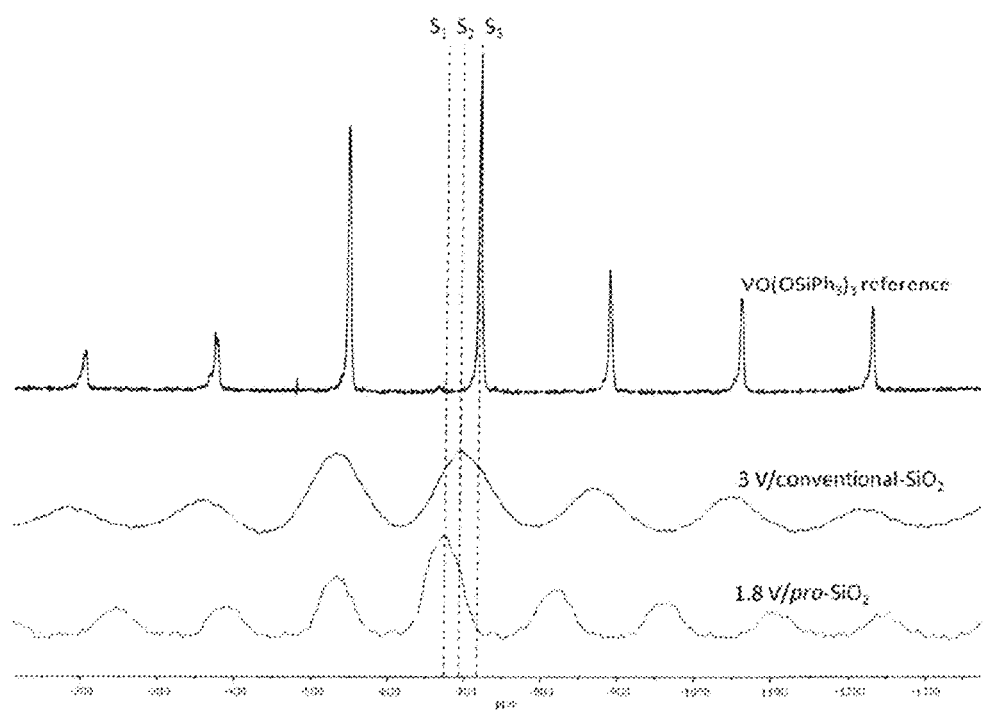

FIG. 20 shows $^{51}$V MAS NMR spectra of supported vanadia on pro-SiO$_2$, conventional-SiO$_2$, and a compared reference material VO(OSiPh3)$_3$. Three isotropic shifts are present, each owing to a four-coordinate, tetrahedral vanadia species: −675 ppm (S$_1$, 1.8V/pro-SiO$_2$), −694 ppm (S$_2$, 3V/conventional-SiO$_2$), −720 ppm (S$_3$, VO(OSiPh$_3$)$_3$ reference). This slight downfield shift upon promotion of Na$^+$ could point to a weak (long distance) interaction between vanadia and sodium promoter.

Figure 21:
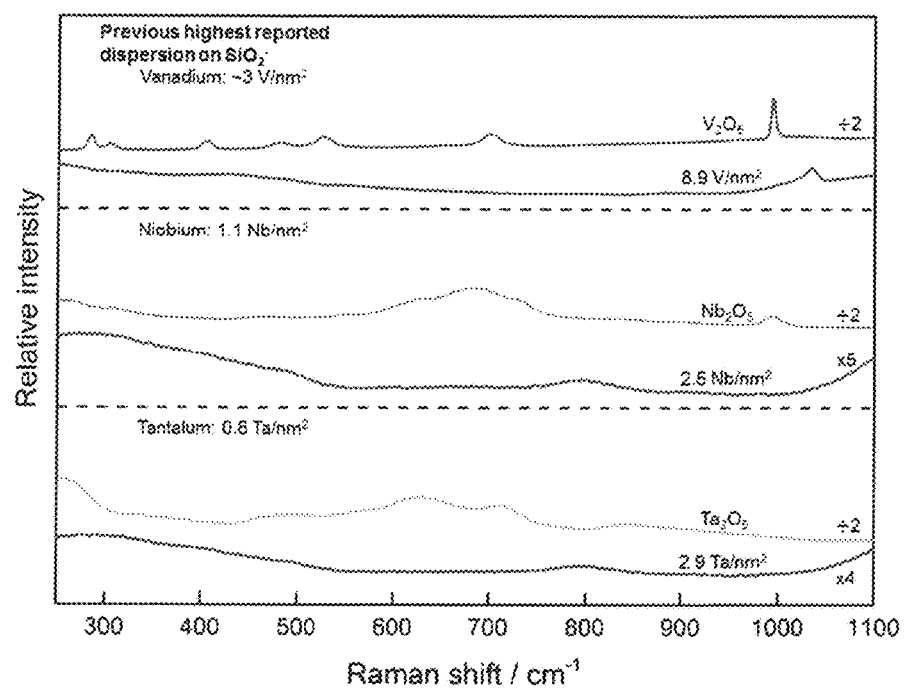

FIG. 21 shows Raman spectra of supported V-oxide and bulk V$_2$O$_5$ (top), supported Nb-oxide and bulk Nb$_2$O$_5$ (middle), and supported Ta-oxide and bulk Ta$_2$O$_5$ (bottom).

Figure 22:
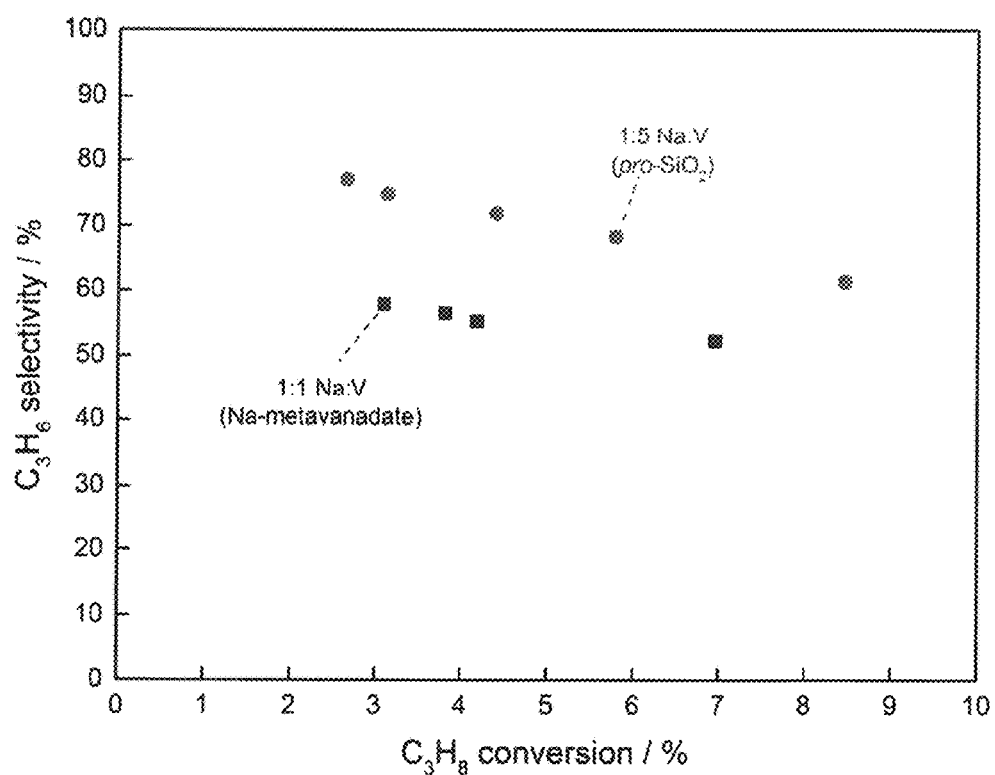

FIG. 22 shows the selectivity to propylene plotted as a function of propane conversion for supported vanadia catalysts with Na/V molar ratios of 0.2 (blue, circle) and 1.0 (black, square). Catalysts containing Na/V>1 was shown to contain Na-metavanadate.

Figure 23:
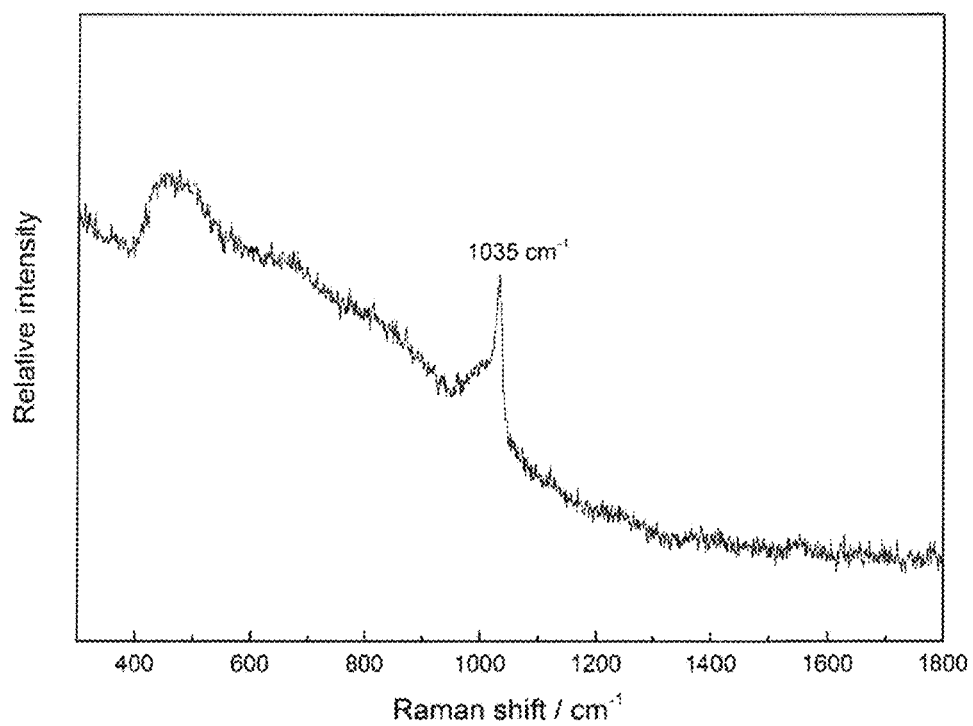

FIG. 23 Raman spectra of a spent 2D vanadia catalyst on pro-SiO$_2$ (7.1 V nm$^{-2}$) under dehydrated conditions (500° C., flowing He). The Raman band attributed to the 2D V=O stretching is preserved after being exposed to reaction conditions while neither 3D V$_2$O$_5$ bands nor Raman bands corresponding to coke deposition can be identified.

Figure 24:
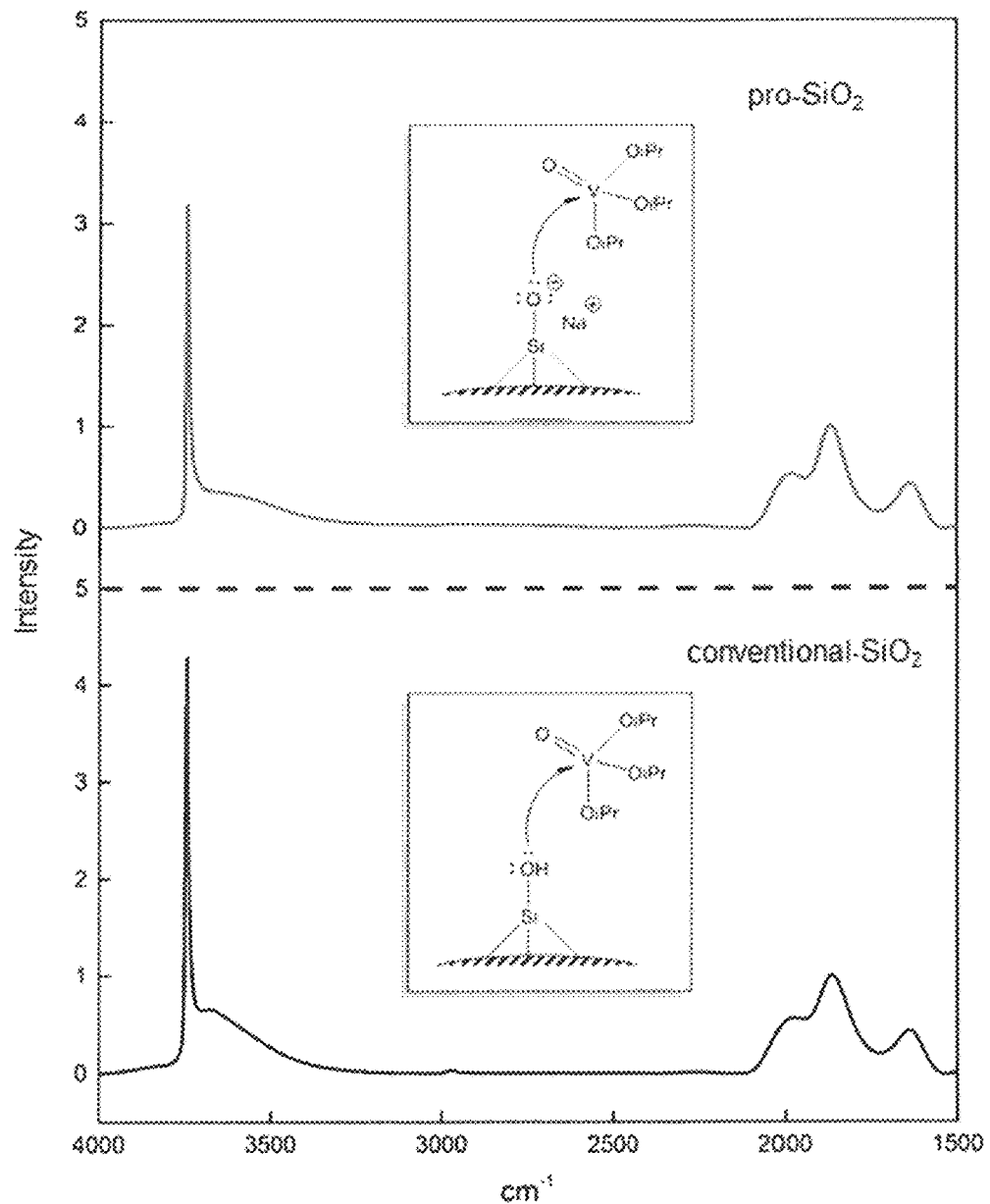

FIG. 24 shows Infrared spectra of pro-SiO$_2$ (top) and conventional-SiO$_2$ (bottom) normalized to the signals of siloxane bridges at 1900 cm$^{-1}$. Lower intensities of the silanol and hydrogen bonding between silanol groups (3745 and 3660 cm$^{-1}$, respectively) in the pro-SiO$_2$ spectra supports higher concentrations of deprotonated silanol groups (Si—O$^-$) in pro-SiO$_2$.

Figure 25:
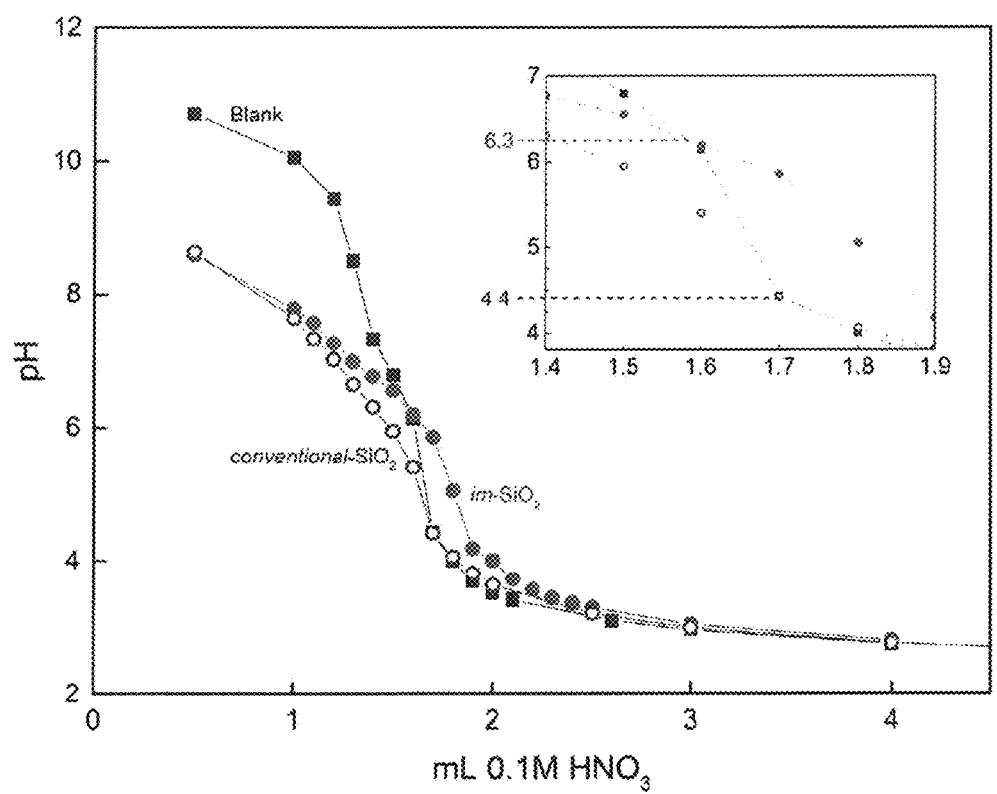

FIG. 25 shows Point zero charge (PZC) analysis of im-SiO$_2$ and conventional-SiO$_2$ compared to a blank solution without SiO$_2$. Samples containing im-SiO$_2$ and conventional-SiO$_2$ each contained 50 mg of SiO$_2$. Intersection between the sample containing im-SiO$_2$ and the blank solution occurs at a higher pH (pH=6.3) than the intersection of the blank with conventional-SiO$_2$ (pH=4.4). This is an indication of im-SiO$_2$ containing a higher concentration of Si—O$^-$ sites than conventional-SiO$_2$.

Figure 26:
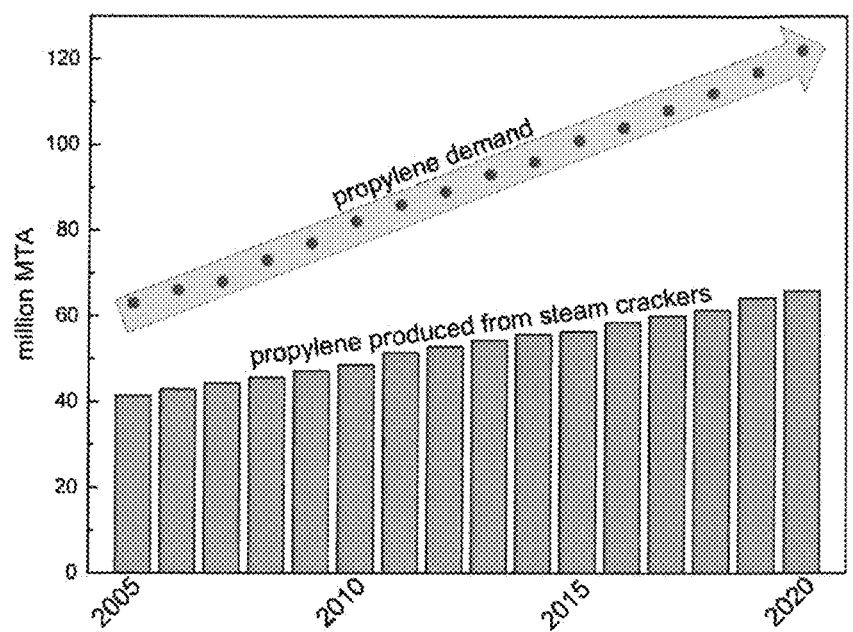

FIG. 26 shows the demand for propylene is growing much more rapidly than it can be produced from steam crackers, creating opportunities for on-purpose production technologies [3].

Figure 27:
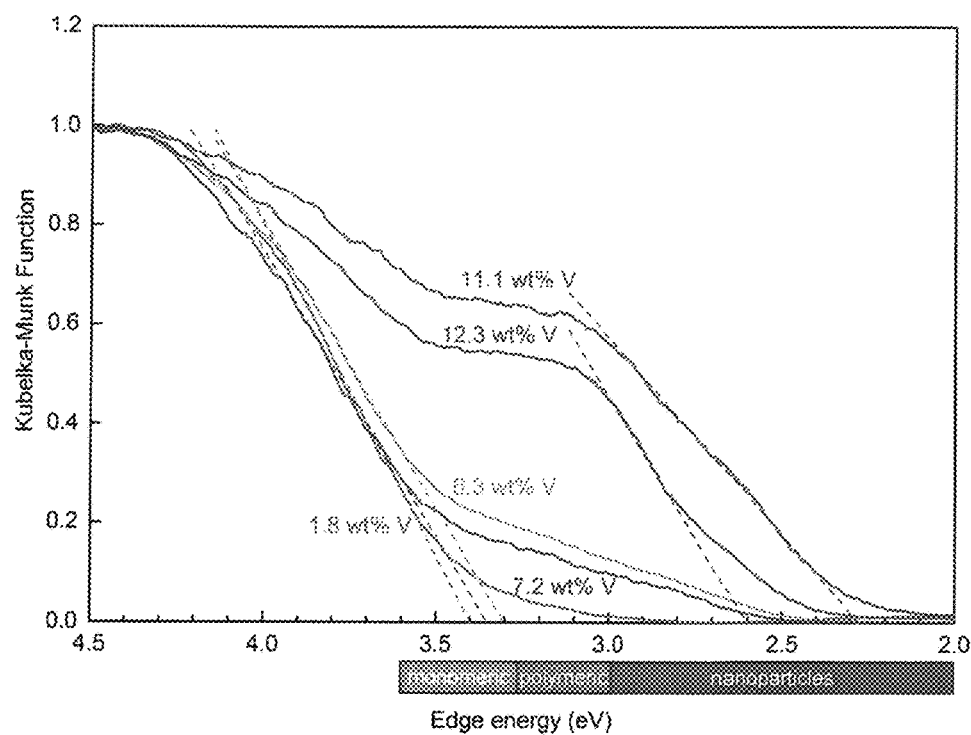

FIG. 27 shows DR-UV-V is spectra of various V/pro-SiO$_2$ samples, differentiating between materials featuring only highly dispersed, monomeric vanadia species, and materials containing V$_2$O$_5$ particles.

Figure 28:
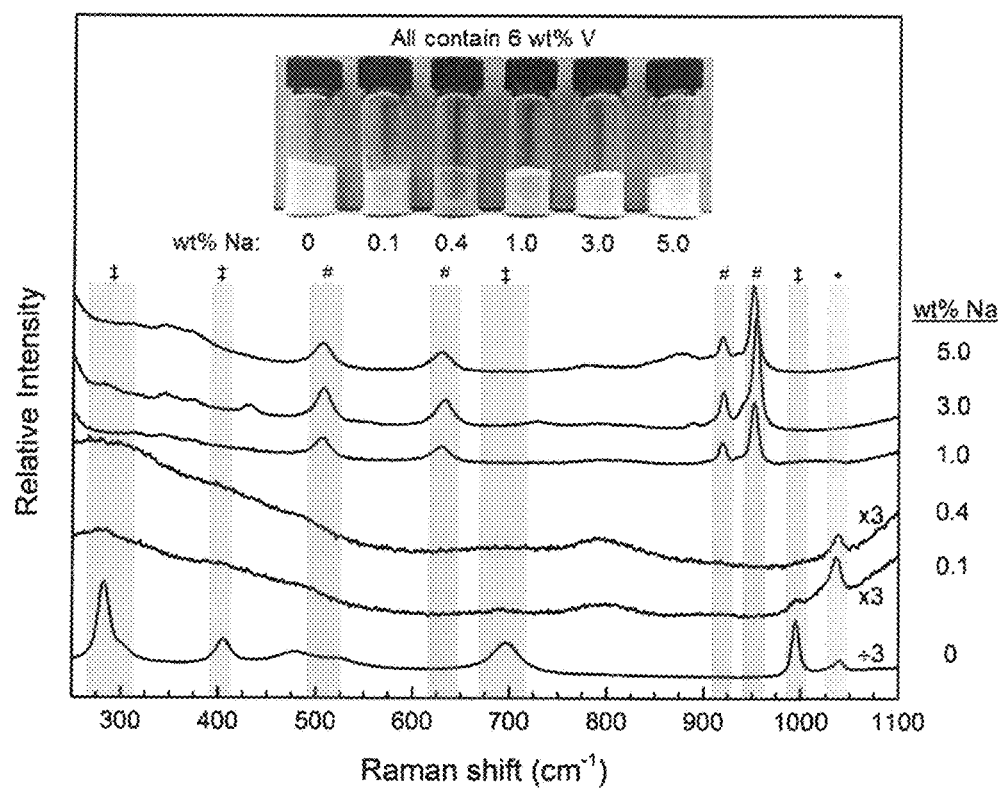

FIG. 28 shows Raman spectra of V/pro-SiO$_2$ with varying Na-content, with all catalysts containing 6 wt % V. Signals marked in green (*) correspond to the V=O stretching of dispersed vanadia species, while those marked in red (‡) are V=O stretching of 3D V$_2$O$_5$. Signals marked in blue (#) are attributed to the formation of sodium metavanadate. The insert is a photograph of the various materials, showing the differences in color.

Figure 29:
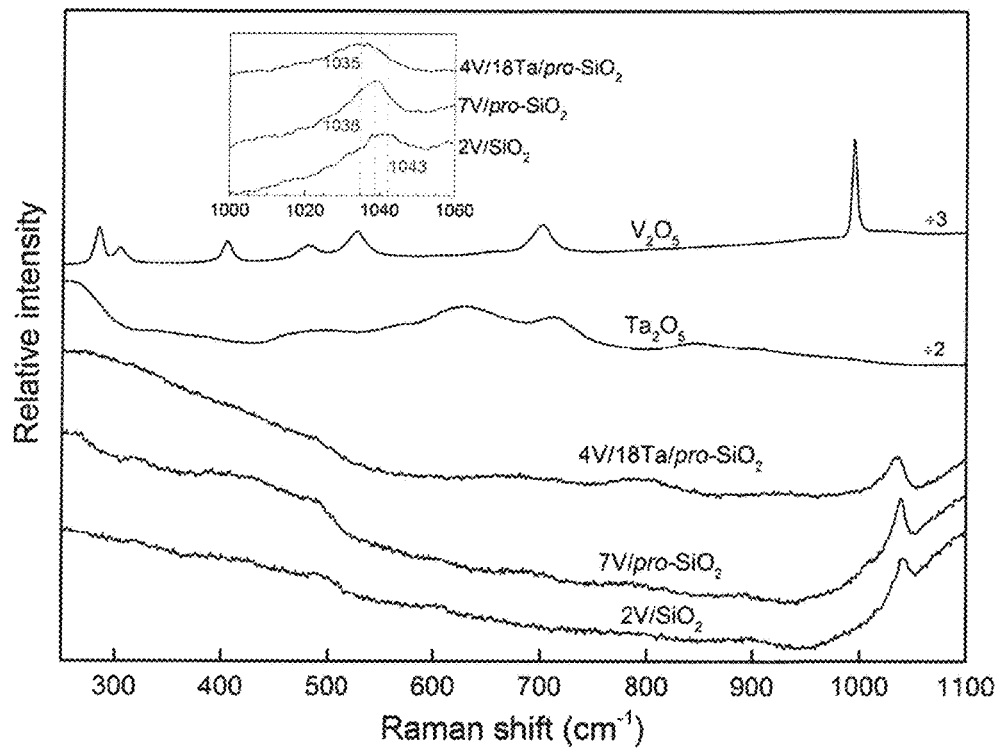

FIG. 29 shows Raman spectra of the V/SiO$_2$ (2 wt % V), V/pro-SiO$_2$ (7 wt % V) and V/Ta/pro-SiO$_2$ (4 wt % V, 18 wt % Ta) materials, compared with the Raman spectra of the bulk V$_2$O$_5$ and Ta$_2$O$_5$ oxides. All supported metal oxides feature 2D species, showing no bands corresponding to 3D V$_2$O$_5$ or Ta$_2$O$_5$ nanoparticles.

Figure 30:
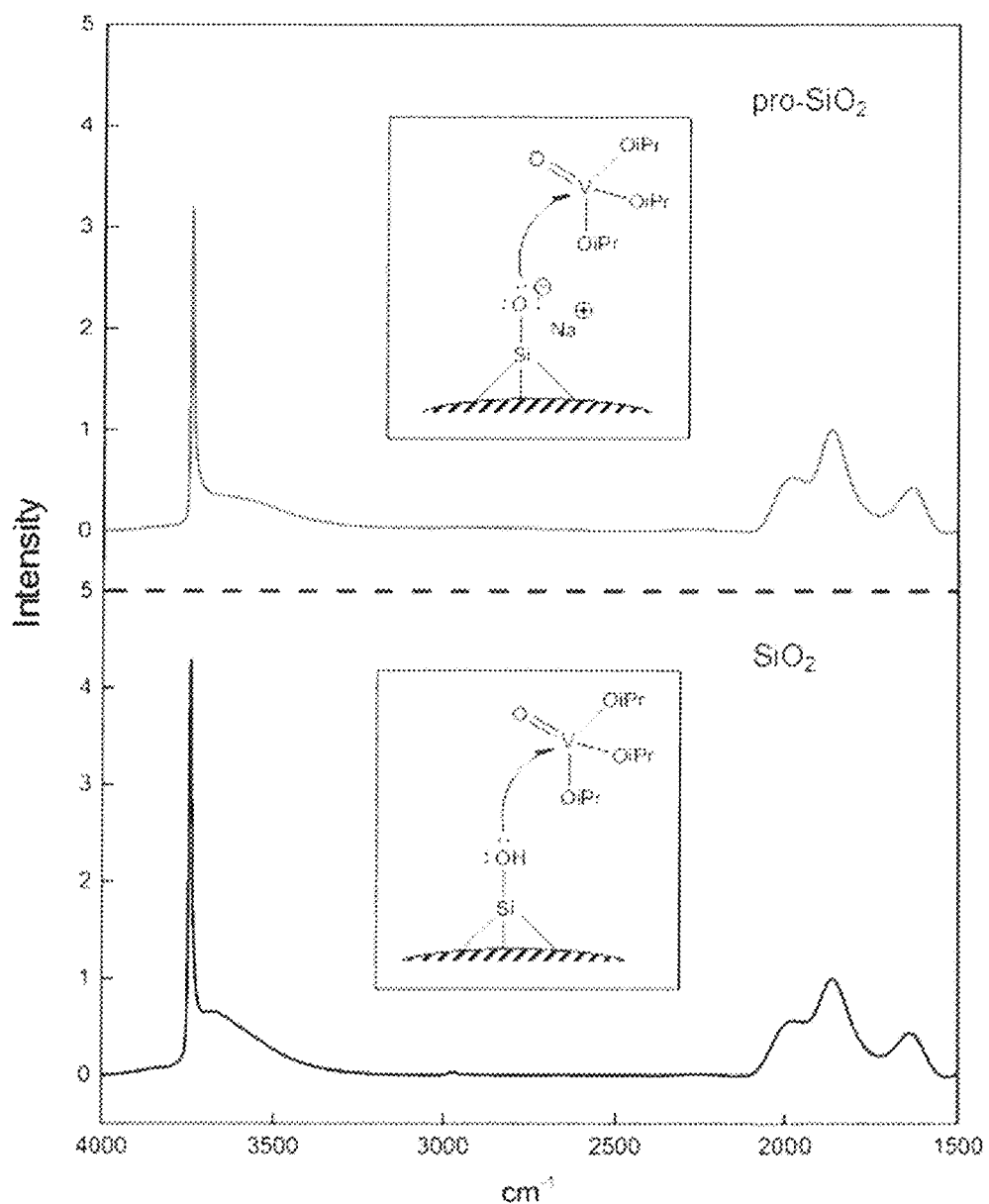

FIG. 30 shows the transmission IR spectra of pro-SiO$_2$ (top) and SiO$_2$ (bottom) normalized to the signals of siloxane overtones at 1900 cm$^{-1}$. We emphasize the lower intensities of the silanol and hydrogen bonded silanol nests (sharp signal at 3745 and broad signal around 3660 cm$^{-1}$, respectively) in case of the pro-SiO$_2$.

Figure 31:
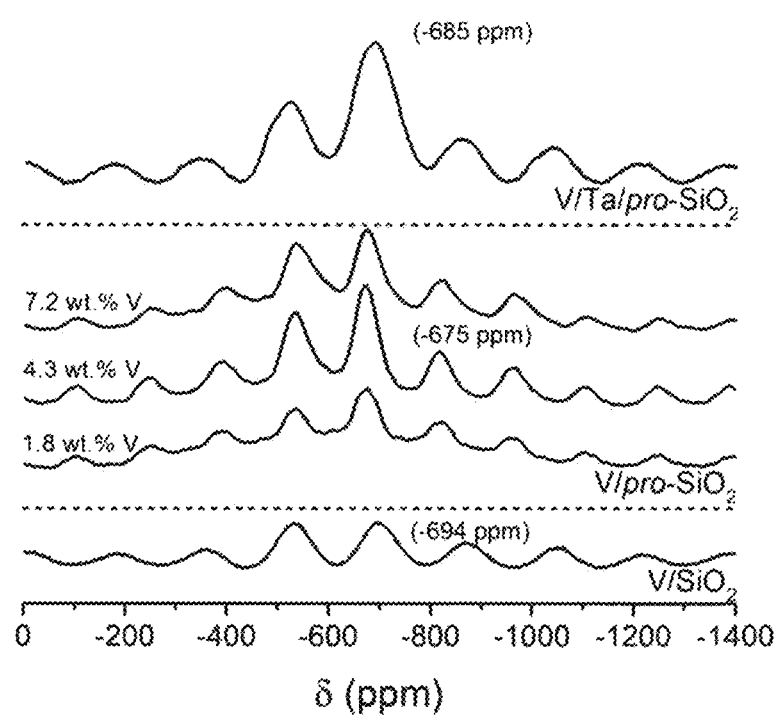

FIG. 31 shows $^{51}$V MAS NMR spectra of V/SiO$_2$ (3 wt % V), various V/pro-SiO$_2$ samples (1.8-7.2 wt % V) and the ternary V/Ta/SiO$_2$ sample.

Figure 32:
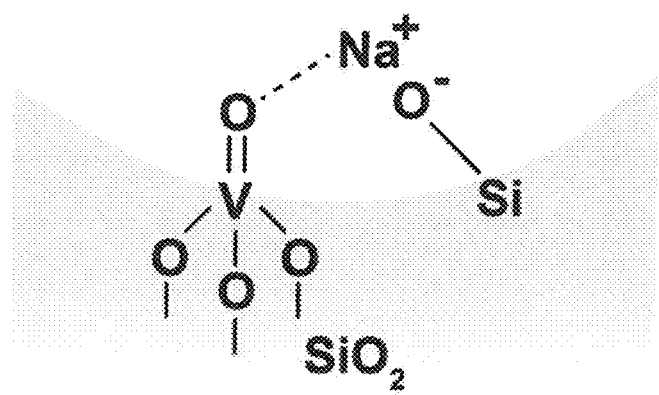

FIG. 32 shows the working hypothesis for the interaction of the sodium with the vanadyl oxygen atom, leading to a slightly weaker V=O bond and a more positive vanadium nucleus.

Figure 33:
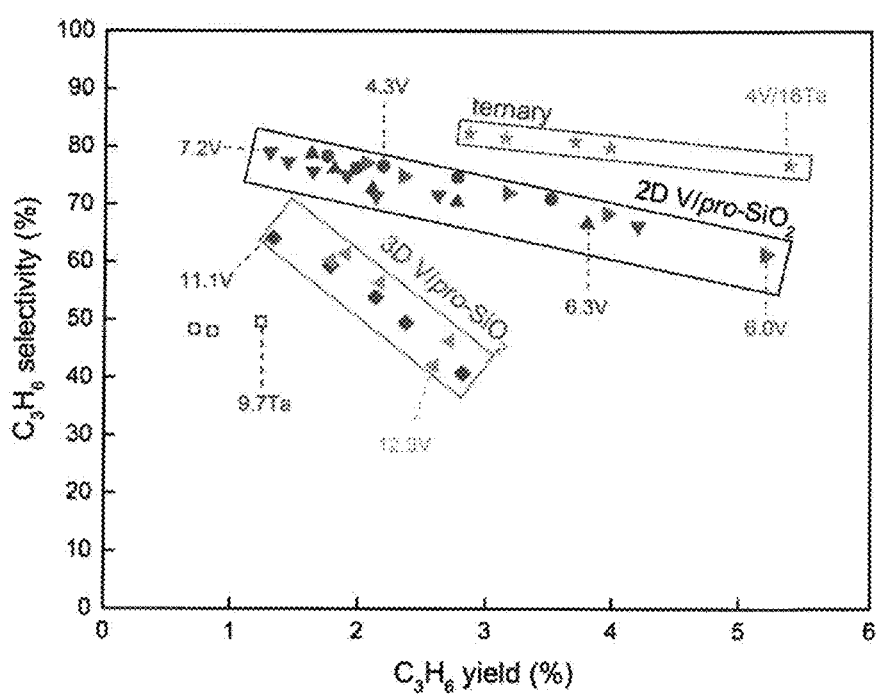

FIG. 33 shows the propylene selectivity (y-axis) as a function of the propylene yield (x-axis) for V/pro-SiO$_2$ catalysts. Catalysts are labeled with their supported metal loadings (wt %).

Figure 34:
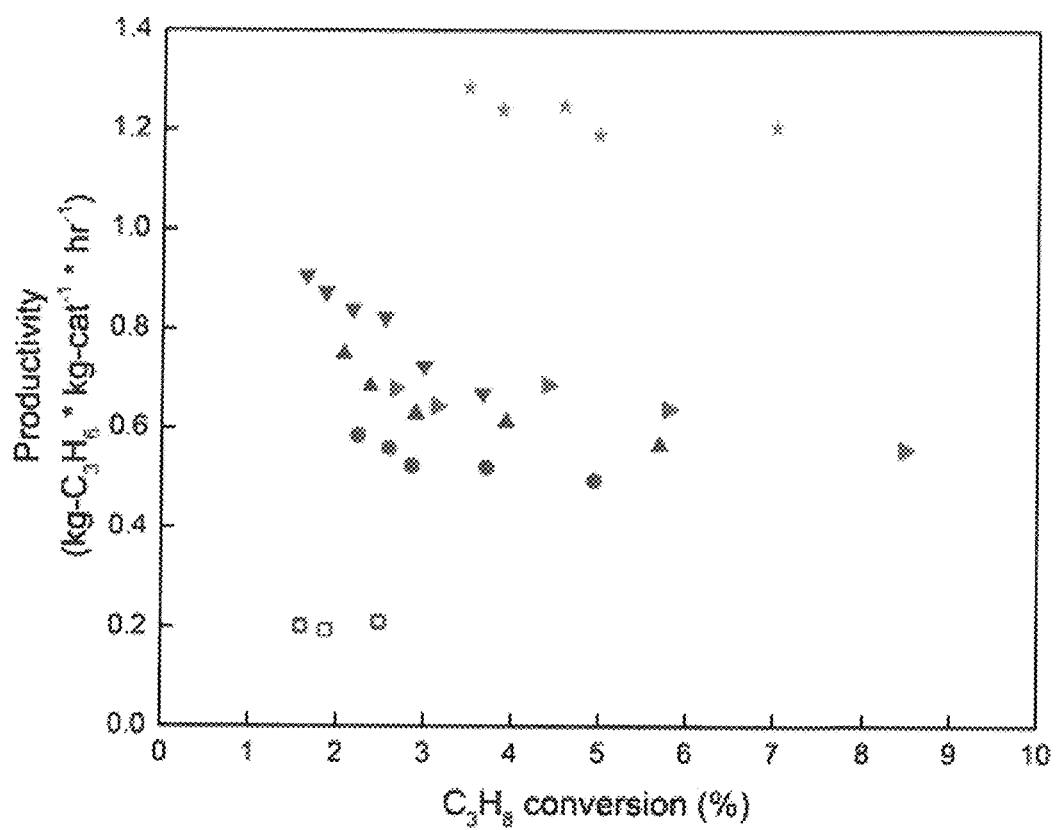

FIG. 34 shows propylene selectivity (y-axis) as a function of the propylene yield (x-axis) for V/pro-SiO$_2$ catalysts. Catalysts are labeled with their supported metal loadings (wt %).

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

I. In General

Before the present materials and methods are described, it is understood that this invention is not limited to the particular methodology, protocols, materials, and reagents described, as these may vary. It is also to be understood that the terminology used in this disclosure is for the purpose of describing particular embodiments only, and is not intended to limit the scope of the present invention, which will be limited only by the language of the appended claims.

As used in this disclosure and in the appended claims, the singular forms "a", "an", and "the" include plural reference unless the context clearly dictates otherwise. The terms "a" (or "an"), "one or more" and "at least one" can be used interchangeably. The terms "comprising". "including", and "having" can also be used interchangeably.

Unless defined otherwise, all technical and scientific terms used in this disclosure have the same meanings as commonly understood by one of ordinary skill in the art to which this disclosure belongs. All publications and patents specifically mentioned in this disclosure are incorporated by reference for all purposes, including for describing and disclosing the chemicals, instruments, statistical analysis and methodologies which are reported in the publications which might be used in connection with the disclosed methods and devices. All references cited in this disclosure are to be taken as indicative of the level of skill in the art.

II. The Invention

This disclosure is based on the inventors' surprising discovery that the use of a sodium ion promoter (and optionally, an aluminum ion co-promoter) on a silica ($SiO_2$) support facilitates the loading of highly dispersed two-dimensional metal oxide species onto the surface of the silica support, without the formation of undesirable nanoparticles. Specifically, we demonstrate in the Examples below that catalysts comprising $Na^+$ promoted silica are capable of exhibiting metal oxide dispersion densities greater than the previously reported maximum dispersion densities for several different metal oxides, including vanadium oxide, niobium oxide, tantalum oxide, and titanium oxide. Given the data presented herein, similarly increased dispersion on $Na^+$ promoted silica would be expected for other group 3, group 4, group 6, and group 7 metal oxides. The increased dispersion of the two-dimensional metal oxide species on the silica support results in a catalyst that can more efficiently catalyze one of the reactions of interest, because there are more active sites present in a given support surface area.

There are a number chemical processes for which the improved catalysts could be used. Examples of reactions of interest include, without limitation: (1) oxidative dehydrogenation of alkanes to olefins using, for example, supported V-oxides; (2) non-oxidative dehydrogenation of alkanes to olefins using, for example, supported Cr-, Mo-, V-, and/or Zn-oxides; (3) alkane oxidation to oxygenates, using, for example, supported Mo- and/or Fe-oxides; (4) olefin metathesis using, for example, supported W-, Mo-, and/or Re-oxides; (5) destruction of chlorocarbons and warfare agents using, for example, supported Nb-oxides; (6) glycerol conversion (to acrolein) using, for example, supported Nb- and/or W-oxides; (7) alkane metathesis using, for example, supported Ta-oxides; (8) ethanol dehydrogenation using, for example, supported Nb-oxides; (9) hydrotreating (a refinery process of reducing sulfur, nitrogen, and/or aromatics content) using, for example, supported Mo-oxides; and (10) partial oxidation using, for example, supported Mo-oxides.

The disclosed catalysts are not limited to the use of a single metal oxide, and encompass supported ternary metal systems as well. Non-limiting examples include the V/Ti/$SiO_2$ or V/Ta/$SiO_2$ systems commonly used to catalyze dehydrogenation of alkanes.

The following Examples are offered for illustrative purposes only, and are not intended to limit the scope of the invention in any way. Indeed, various modifications of the invention in addition to those shown and described herein will become apparent to those skilled in the art from the foregoing description and the following Examples and fall within the scope of the appended claims.

III. Examples

Example 1: Enhanced Dispersion of Vanadium Oxide on an $SiO_2$ Support Comprising an $Na^+$ Dispersion Promoter Synthesis of Vanadium Oxide Catalysts Supported on $Na^+$-Promoted $SiO_2$ Promoted $SiO_2$ was synthesized using incipient wetness impregnation and subsequent calcination, using $Na(NO_3)$ and $Al(NO_3)_3$ as metal precursor solutions. Appropriate amounts of $Na(NO_3)$ and $Al(NO_3)_3$ solutions, enough to support 0.40 wt % $Na^+$ and 0.09 wt % $Al^{3+}$ on the $SiO_2$, were diluted in deionized water to equal the pore volume of the $SiO_2$ support. Specifically, the metal precursor solution was prepared using 0.35 mL of 1M $NaNO_3$, 0.33 mL of 0.2M $Al(NO_3)_3$, and 1.93 mL deionized $H_2O$ per 2 g of $SiO_2$, culminating in 0.40 wt % $Na^+$ and 0.09 wt % $Al^{3+}$ in the final promoted-$SiO_2$ sample. This solution was then dripped onto the $SiO_2$, using a mortar and pestle to ensure proper contact between metal precursor solution and the oxide support. The resulting composition was then placed into a calcination furnace and heated to 700° C., ramping 1.5° C./min under flowing air, and holding at 700° C. for 4 hours, also under flowing air.

Vanadium oxide supported catalysts were made from the resulting Na-promoted $SiO_2$ by a second incipient wetness impregnation and subsequent second calcination. Specifically, six different precursor solutions comprising the vanadium oxide precursor vanadium oxytriisopropoxide and isopropyl alcohol were prepared, using vanadium oxide precursor concentrations calculated to result in a wt % V on the $SiO_2$ support of 1.8, 4.3, 6.3, 7.2, 11.1 and 12.3, respectively. These concentrations would result in a vanadium surface density of 1.3, 4.1, 7.2, 8.9, 13.4, and 15.4 $V_{atoms}/nm^2$, respectively. Surface density is calculated using the following formula:

Surface density, $(M)/nm^2$ $$\text{surf density} = \frac{\text{wt \%  } M \times 6.02 \times 10^{23}}{MW_M \times \text{surf area} \times 10^{18}}$$

where $MW_M$=molecular weight of metal, M (g/mol)
wt % M=loading of metal, M (%)
surf area=surface area of catalyst ($m^2$/g)

Each of the precursor solutions were dripped onto the $Na^+$-promoted $SiO_2$, using a mortar and pestle to ensure proper contact between metal precursor solution and the oxide support. The resulting vanadium oxide catalyst compositions were then placed into a calcination furnace and heated to 700° C., ramping 1.5° C./min under flowing air, and holding at 700° C. for 3 hours, also under flowing air. The calcined supported vanadium oxide catalysts were then tested for enhanced metal oxide dispersion and catalytic activity.

Enhanced Dispersion of Vanadium Oxide Catalysts Supported on $Na^+$-Promoted $SiO_2$.

Figure 4:
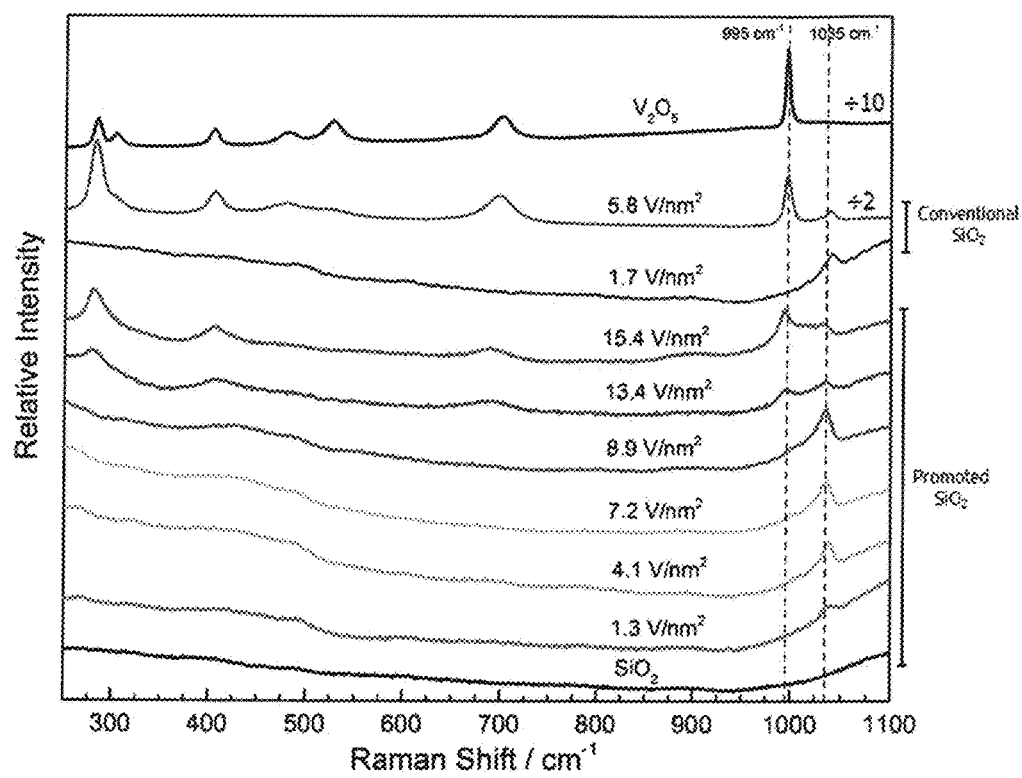
FIG. 4 is a compilation of Raman spectra (785 nm laser source) at various loadings of vanadium oxide on silica. The peaks at 1035 and 995 cm-1 correspond to the V=O stretching vibration of dispersed and nanoparticle species, respectively. Other peaks exist for nanoparticle $V_2O_5$, at 700, 520, 500, 400, and 300 cm$^{-1}$. The $V_2O_5$ nanoparticle peaks appears above 1.7 V/nm$^2$ for unpromoted $SiO_2$, in agreement with previous literature. Using Na$^+$ promoted $SiO_2$, as shown by the nanoparticle peaks only appearing above the 8.9 V/nm$^2$ loading density.

The enhanced dispersion of vanadium oxide on $Na^+$-promoted $SiO_2$ was demonstrated through Raman spectroscopy and UV-vis spectroscopy. FIG. 4 shows a compilation of Raman spectra (785 nm laser source) at various loadings of vanadium oxide on silica. The peaks at 1035 and 995 cm-1 correspond to the V=O stretching vibration of dispersed and nanoparticle species, respectively. Other peaks exist for nanoparticle $V_2O_5$, at 700, 520, 500, 400, and 300 $cm^{-1}$. The $V_2O_5$ nanoparticle peaks appears above 1.7 $V/nm^2$ for unpromoted $SiO_2$, in agreement with previous literature. However, when using $Na^+$-promoted $SiO_2$, the nanoparticle peaks only appear above the 8.9 $V/nm^2$ loading density (i.e., 13.4 and 15.4 $V/nm^2$). This data demonstrates successful nanoparticle-free dispersion of vanadium oxide at dispersion densities almost three times greater than previously reported.

Analysis of UV-visible spectroscopy agrees with nanoparticle assignments of supported vanadium-oxide on promoted silica. The specific UV-vis edge energy shift of each supported vanadium-oxide catalyst is shown in Table 1. UV-vis edge energies of catalysts below monolayer vanadium-oxide coverage (<8.9$V/nm^2$) show edge energies of ~3.6 eV, corresponding to the support being entirely comprised of tetrahedral $VO_4$ sites. Only the highest loadings of vanadium-oxide (13.4 and 15.4 $V/nm^2$), meanwhile, show edge energies <3.0 eV, corresponding to the existence of nanoparticle $V_2O_5$ found on the $SiO_2$ surface.

Catalytic Activity of Vanadium Oxide Catalyst Supported on $Na^+$-Promoted $SiO_2$.

Figure 1:
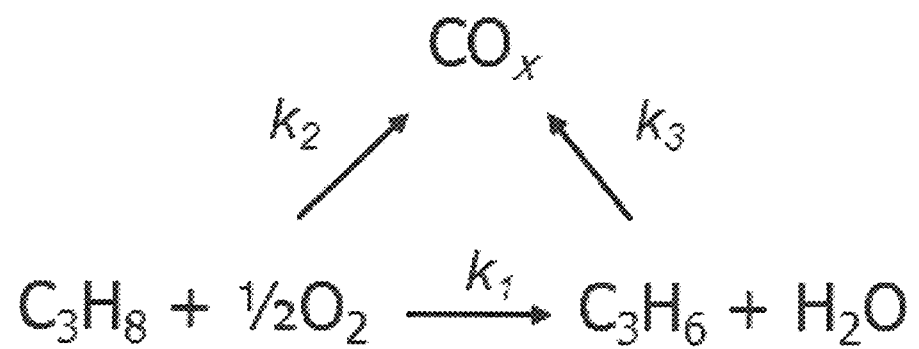
FIG. 1 shows the chemical equation representing oxidative propane dehyogenation (ODHP), a chemical process that can be catalyzed by the disclosed supported metal oxides. $k_1$ is the rate constant of the desired production of propylene from propane, while k2 and k3 are the rate constants for the combustion of reactant and product, respectively, to form $CO_x$, a competing side reaction that decreases the efficiency of production of the desired product. The presence of metal oxide nanoparticles on the support surface detrimentally increases the rate of these combustion side reactions.
Figure 2:
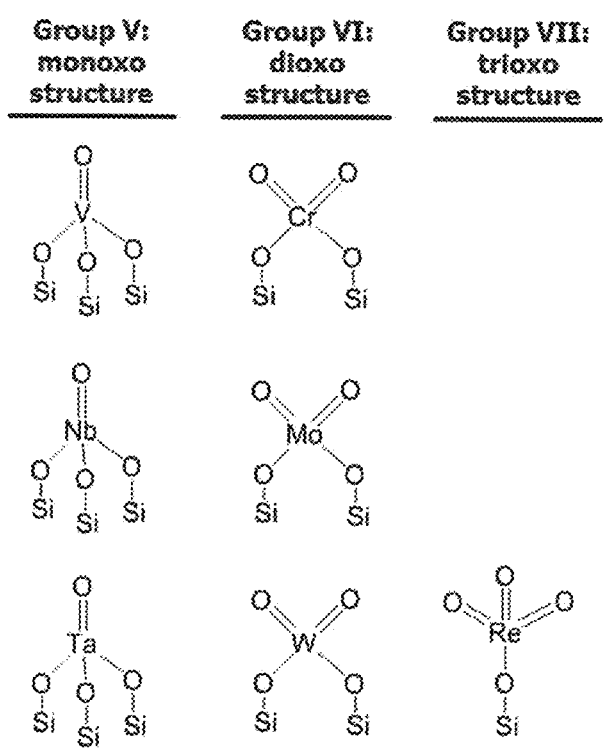
FIG. 2 includes drawings showing the chemical structures of the monomeric forms of exemplary group 5, group 6, and group 7 metal oxides bonded to a silica support. Each of the structures exhibits tetrahedral geometry.
Figure 3:
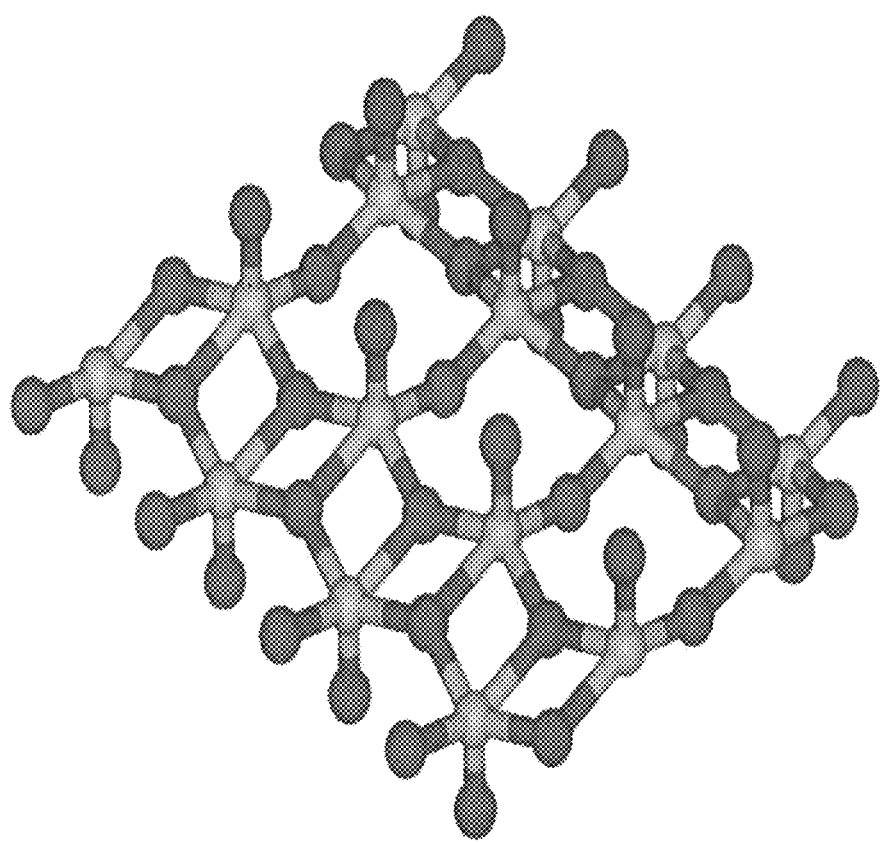
FIG. 3 is a drawing showing the chemical structure of the nanoparticle form of a metal oxide. The structure does not exhibit tetrahedral geometry.
Figure 5:
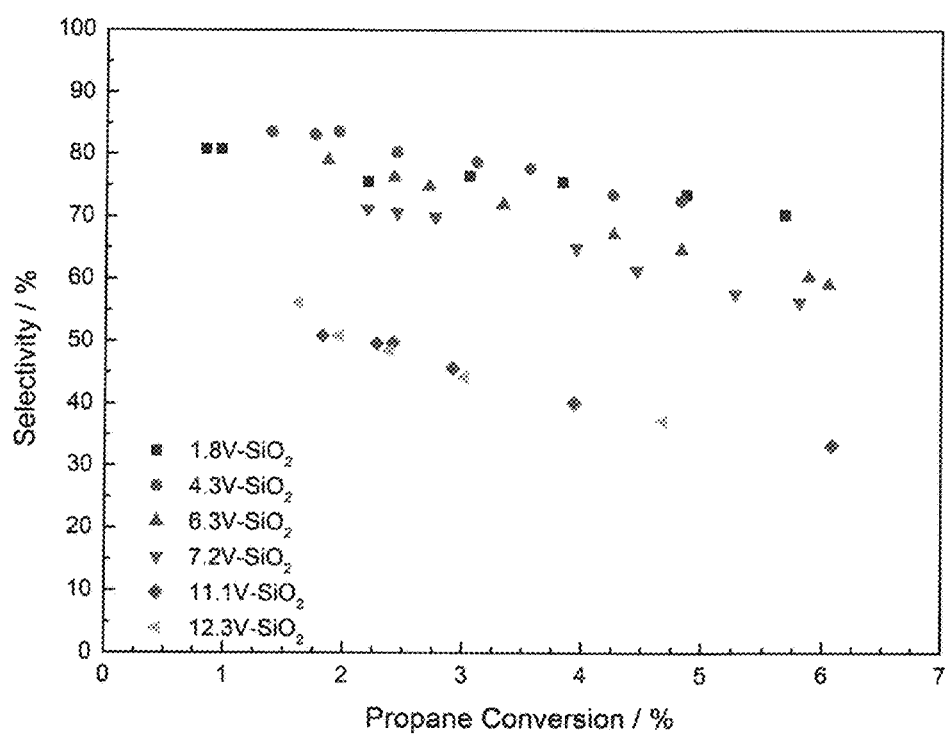
FIG. 5 is a graph of propane conversion vs. selectivity to propylene for ODHP at various loadings of vanadium oxide. The existence of nanoparticle vanadium oxide (found in the two highest vanadium oxide loadings, 11.1 wt % $V_2O_5$ on $SiO_2$ and 12.3 wt % $V_2O_5$ on $SiO_2$) increases the rates of propylene and propane combustion to CO and $CO_2$, thus significantly dropping selectivity to the desired propylene product. This result is consistent with the dispersion data shown in FIGS. 4 and 5.

The activity of the catalysts was assessed in an oxidative propane dehydrogenation reaction (ODHP; see FIG. 1). Propane conversion vs. selectivity to propylene was determined at various loadings of vanadium oxide. As shown in FIG. 5, the existence of nanoparticle vanadium oxide (found in the two highest vanadium oxide loadings, 11.1 wt % V on $SiO_2$ and 12.3 wt % V on $SiO_2$) increases the rates of propylene and propane combustion to CO and $CO_2$ ($k_2$ and $k_3$ in FIG. 1), thus significantly dropping selectivity to the desired propylene product (FIG. 5, lower data points). This result is consistent with the dispersion data shown in FIG. 4.

Notably, we have demonstrated enhanced dispersion of vanadium oxide on $SiO_2$ resulting from the introduction of as little as 160 ppm $Na^+$ to the silica support.

TABLE 1

Chemical composition and UV-vis data for the six vanadium oxide catalysts

| Wt % V on $SiO_2$ | Wt % $V_2O_5$ on $SiO_2$ | Na/V molar ratio | Vanadia surface density [$V_{atom}/nm^2$] | UV-vis edge energy | UV-vis assignment |
|---|---|---|---|---|---|
| 1.8 | 3.2 | 0.49 | 1.3 | 3.5 | monomeric $VO_4$ |
| 4.3 | 7.7 | 0.21 | 4.1 | 3.5 | monomeric $VO_4$ |
| 6.3 | 11.3 | 0.14 | 7.2 | 3.5 | monomeric $VO_4$ |
| 7.2 | 12.9 | 0.12 | 8.9 | 3.6 | monomeric $VO_4$ |
| 11.1 | 19.8 | 0.08 | 13.4 | 2.6 | Nanoparticles |
| 12.3 | 22.0 | 0.07 | 15.4 | 2.9 | Nanoparticles |

Figure 6:
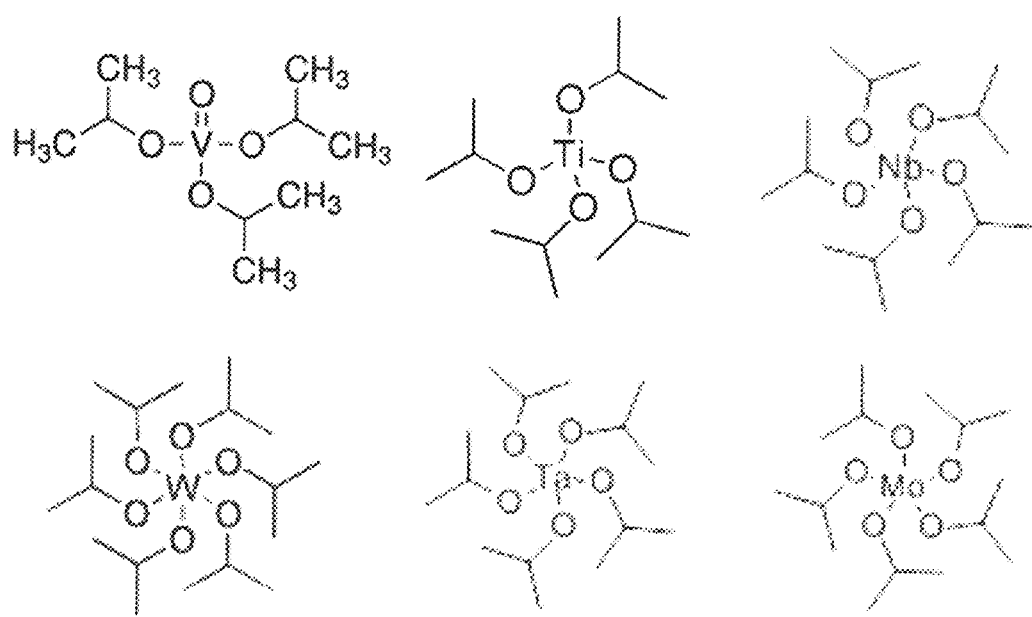
FIG. 6 shows examples of alkoxide precursor chemicals that can be used to make the disclosed catalysts.
Figure 7:
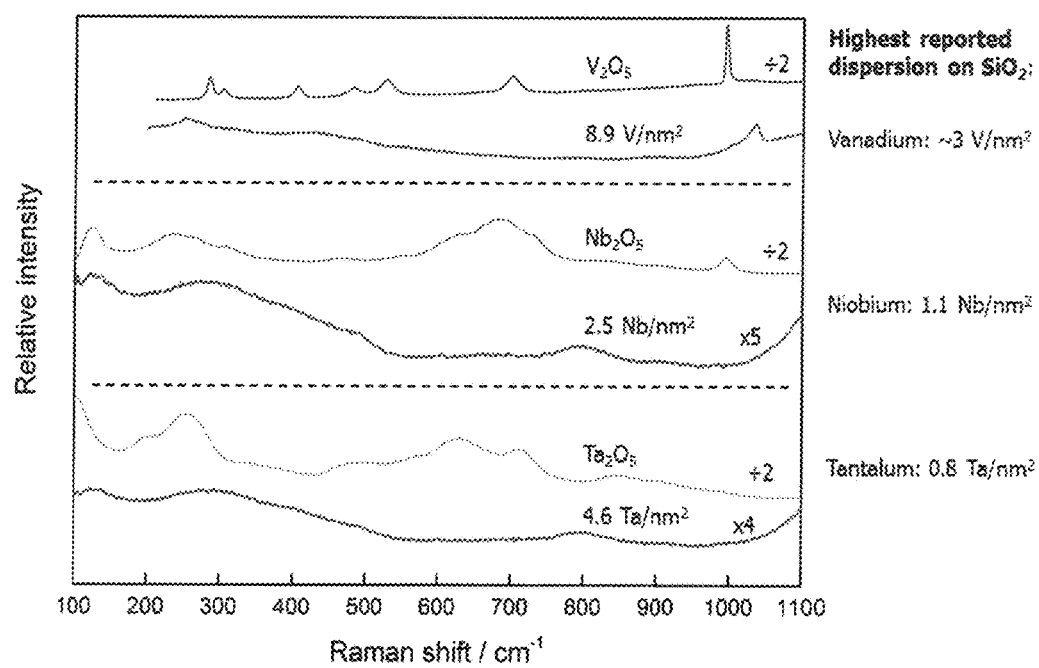
FIG. 7 shows Raman spectra (785 nm laser source) for bulk $V_2O_2$ (top line), for vanadium oxide on Na$^+$-promoted silica at a dispersion density of 8.9 V/nm$^2$ (second line from top), for bulk $Nb_2O_5$ (third line from top), for niobium oxide on Na$^+$-promoted silica at a dispersion density of 2.5 Nb/nm$^2$ (fourth line from top), for bulk $Ta_2O_5$ (fifth line from top), and for tantalum oxide on Na$^+$-promoted silica at a dispersion density of 4.6 Ta/nm$^2$ (bottom line). In each case, the catalyst made using the Na$^+$-promoted $SiO_2$ lacks the characteristic nanoparticle peaks exhibited by the bulk metal oxide materials.

Example 2: Enhanced Dispersion of Other Metal Oxides on an $SiO_2$ Support Comprising an $Na^+$ Dispersion Promoter Using similar procedures to those described in Example 1, we have demonstrated enhanced dispersion on silica surfaces comprising an $Na^+$ promoter using metal oxides other than vanadium oxide, including niobium oxide, tantalum oxide, and titanium oxide. For each of these metal oxides, the alkoxide precursor was used to make the catalyst (see FIG. 6). As shown in the Raman spectra of FIG. 7, niobium oxide loading at a dispersion density of 2.5 $Nb/nm^2$ resulted in successful nanoparticle-free dispersion on the $Na^+$-promoted silica surface, a much higher dispersion density than the previously reported maximum dispersion of 1.1 $Nb/nm^2$. Similarly, tantalum oxide loading at a dispersion density of 4.6 $Ta/nm^2$ resulted in successful nanoparticle-free dispersion on the $Na^+$-promoted silica surface, a far higher dispersion density than the previously reported maximum dispersion of 0.8 $Ta/nm^2$. Similar results were obtained for titanium oxide (data not shown).

As a prophetic extension of this Example, enhanced dispersion of W-oxide and Mo-oxide on $SiO_2$ will be demonstrated. Dispersion of these oxides using Mo and W-alkoxide precursors (see FIG. 7) has not yet been tested. However, based on the data reported for other metal oxides, we expect to demonstrate enhanced dispersion for these metal oxides.

Further testing is planned to further demonstrate the catalytic activity of the disclosed catalysts. As a non-limiting example, an olefin metathesis reaction may be catalyzed, such as propylene metathesis to ethylene and butylene. Alternatively, the reverse reaction, metathesis of butylene and ethylene to form two equivalents of propylene, may be catalyzed.

Further extensions may also include developing "ternary catalysts" (multiple-supported metal oxide catalysts) for ODHP. In a non-limiting example, such ternary catalysts may include one or more group 5 metals, e.g., V/Nb/promoted-$SiO_2$.

Figure 8:
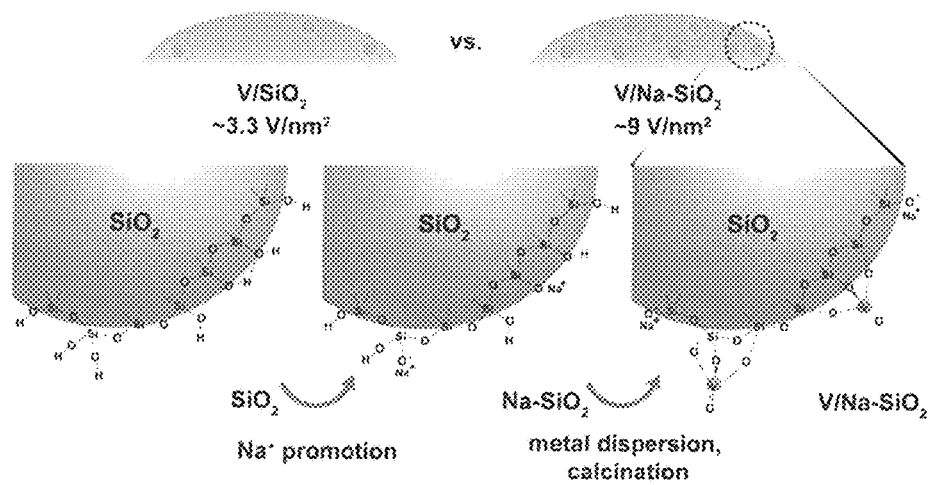
FIG. 8 illustrates alkali metal promotion, metal dispersion, and calcination steps according to the invention.

Example 3: Enhanced Two-Dimensional Dispersion of Group V Metal Oxides on Silica The catalytic performance of supported metal oxides is often controlled by their two- or three-dimensional dispersion. Silica, one of the popular inert supports, triggers the undesired formation of three-dimensional nanoparticles at significantly lower loadings than other conventional supports like $Al_2O_3$, $TiO_2$, $Nb_2O_5$, or $ZrO_2$. This observation has been ascribed to the lower reactivity of surface SiOH groups toward the precursor, compared to other metal hydroxyl groups on different supports. In this contribution, we show that by promoting amorphous silica with low amounts of sodium, the surface density of two-dimensional metal oxide species can be significantly enhanced to the same level as all other oxide supports previously reported in the literature. This effect is demonstrated for the case of supported vanadia using a variety of spectroscopic techniques (i.e., Raman, diffuse reflectance UV-vis, and $^{51}$V-MAS NMR), as well as a catalytic activity study for the oxidative dehydrogenation of propane (ODHP), a structure-sensitive probe reaction. The propane consumption rate was found to increase linearly with the vanadium surface density while the propylene selectivity was not affected until a monolayer coverage of ca. 9 vanadia per $nm^2$ was surpassed. (FIG. 8) The method is also applicable to other group V metals (i.e., Nb- and Ta-oxide), opening new perspectives for supported metal oxides.

Figure 9:
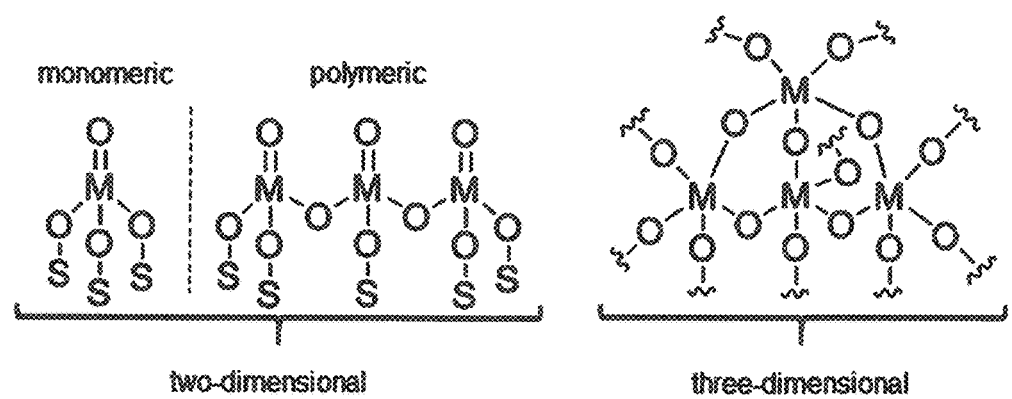
FIG. 9 shows two-(monomeric and oligomeric/polymeric) and three dimensional group V supported metal oxide structures. S=support atom (Si, Al, Ti, etc.), M=supported metal (V, Nb, Ta).

Supported metal oxides are an important class of catalytic materials, used for a variety of important reactions such as alkane oxidation and olefin metathesis, among others. (1,2) The surface structure of such materials is known to control the catalytic performance. (3) Previous work in this area classified supported metal oxide structures as being above or below "monolayer coverage" defined as the maximum amount of twodimensional (2D) metal oxide species that can exist on a support oxide surface before triggering the formation of threedimensional (3D) nanoparticles. (4) Metal oxides below the monolayer exist solely as 2D "dispersed" surface structures and may be present as isolated monomers and/or oligo- or polymeric species, featuring one or more bridging oxygen atoms between the metal centers (M-O-M). FIG. 9 compares monomeric and polymeric 2D structures with that of 3D nanoparticles of supported group V metal oxides.

The oxidative dehydrogenation of propane (ODHP) is a potential alternative for propane dehydrogenation (so-called "on-purpose" propylene production), due to its favorable thermodynamics and negligible coke formation. Yet, the low propylene selectivity restricts its industrial implementation, despite the potential for significant energy savings. Though varieties of catalysts have been explored for ODHP, supported vanadia catalysts have shown some of the most interesting results. While the desired dehydrogenation pathway is suggested to be structure-independent, the competing side-reactions, i.e. propylene (and to a lesser extent, propane) overoxidation to $CO_x$, becomes more favored over $V_2O_5$ nanoparticles. (15,35) Thus, in order to improve the propylene productivity, catalysts must maximize two-dimensional dispersion.

Figure 10:
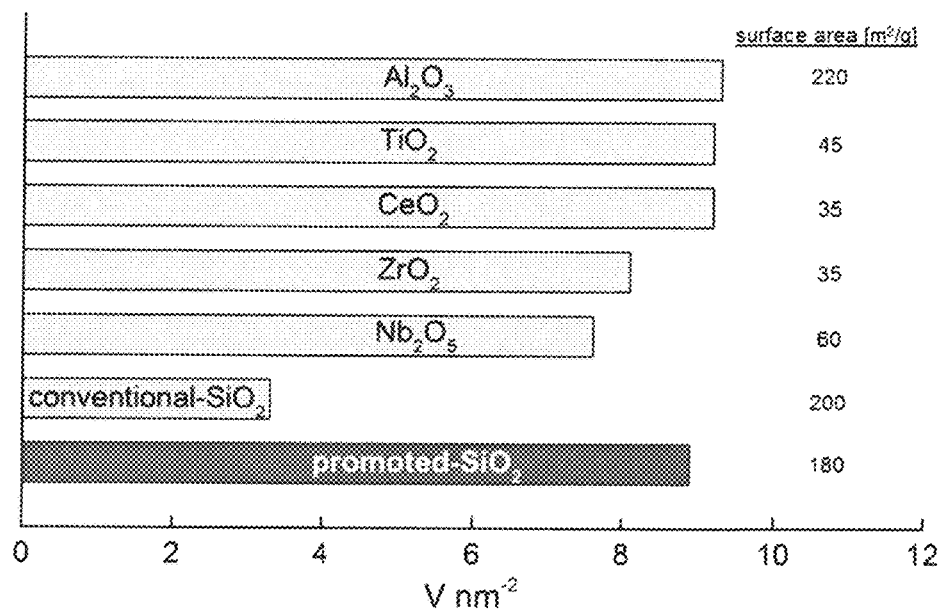
FIG. 10 shows experimental coverages of 2D vanadia species (in V nm$^{-2}$) on various oxide supports and their representative surface areas.

It is well established that the oxide support influences the catalytic activity, mainly due to intrinsic acid/base properties of the support. (35) Silica ($SiO_2$) is one of the most utilized oxide supports, due to its low cost and inert properties. However, up until now, $SiO_2$ only allows a low surface density of supported metal oxides to exist as 2D species compared to all other oxide supports, despite its high surface area. This is well documented in the case of supported vanadia (FIG. 10), which can exist as 2D species up to ~7-9 vanadium atoms per square nanometer (V $nm^2$) on various oxide supports, except for $SiO_2$, which only allows up to 3.3 V $nm^2$, irrespective of the synthesis protocol. This anomaly has previously been attributed to the low reactivity of surface hydroxyl groups on $SiO_2$, resulting in less favorable vanadia anchoring to the $SiO_2$ surface. Greater metal oxide dispersion on $SiO_2$ could serve to increase the density of active sites, thus increasing the space-time yield, as well as to investigate synergetic effects between various surface species in close proximity (viz., synergetic effects in combined monolayer materials).

In this study, we show that the optimal addition of sodium as a promoter can increase the level of dispersion of group V metal oxides on $SiO_2$ to be equivalent to that of other oxide support materials. This is demonstrated by a variety of characterization techniques, including Raman spectroscopy, diffuse reflectance UV-vis, and $^{51}V$ MAS NMR. Further, ODHP is utilized as a structure-sensitive probe reaction: increasing the 2D vanadia dispersion serves to linearly increase space-time yield while maintaining the same selectivity to propylene.

Catalyst Preparation.

Impure silica (im-$SiO_2$) was used as provided by the supplier (Sigma-Aldrich; 165 $m^2$ $g^{-1}$; batch #MKBN2949 V) without any further treatment. $Na^+$ promoted $SiO_2$ (pro-$SiO_2$) was prepared by incipient wetness impregnation of conventional amorphous silica (Aerosil200 from Evonik; 200 $m^2$ $g^{-1}$) by a sodium nitrate solution, followed by calcination under air. An appropriate amount of 1 M $Na(NO_3)$ solution was diluted in deionized $H_2O$ to equal the pore volume of the Aerosil200 (1.3 mL $g^{-1}$). This sample was then calcined under air, ramping 1.5° C. min-1 to 700° C., and holding at 700° C. for 4 h. The optimal pro-$SiO_2$ material contains 0.40 wt % $Na^+$ and shows a surface area of 180±5 $m^2$ $g^{-1}$. Nitrate salts of alternative alkali or alkaline earth metals (Li-, K-, Rb-, Mg-nitrate) were used to attempt to substitute $Na^+$. Their methods of preparation are identical to that described for pro-$SiO_2$. The order of impregnation, whether it be V/alkali/support or alkali/V/support, and the consequences it may have on catalytic activity were previously studied. This work suggested stronger alkali-support interaction with an initial alkali impregnation in case of alumina support. This resulted in more active vanadia species but did not address the influence on the metal oxide dispersion.

All supported metal oxide catalysts were synthesized via incipient wetness impregnation, following previously reported synthesis procedures for analogous materials. Prior to impregnation, im-$SiO_2$, pro-$SiO_2$, or conventional-$SiO_2$ was dried under static conditions overnight at 120° C. Impregnation was performed inside a glovebox under a dry N2 atmosphere. Metal alkoxide solutions, i.e., vanadium oxytriisopropoxide (VTI; Sigma-Aldrich), niobium ethoxide (Sigma-Aldrich, 99.95%), and tantalum ethoxide (Sigma-Aldrich, 99.98%), were used as the metal oxide precursors. Those alkoxide precursors were previously shown to be superior to other precursors like sodium metavanadate and the like. The alkoxides were diluted with dry isopropanol (Sigma-Aldrich, 99.5%) or dry ethanol (Sigma-Aldrich, 99.5%) prior to impregnation to form a solution equal in volume to the pore volume of the support. The ratio of metal-to-isopropanol was altered to create a variety of metal oxide loadings. Impregnated samples were vacuum-dried inside the glovebox and transferred to a calcination oven where they were dried under a flow of $N_2$ at 120° C. for 3 h, ramped to 550° C. at 1° C. min-1 under dry air, and calcined at 550° C. for 3 h. Catalyst Characterization. Raman measurements were carried out with a Renishaw InVia Raman Spectrometer with a 785 nm excitation laser. All measurements used a 1200 L $mm^{-1}$ grating and were taken with a range of 250-1200 $cm^{-1}$ and a dispersion of 1.36565 $cm^{-1}$ $pixel^{-1}$. The experiments were performed in a high-temperature Linkam CCR1000 cell. Samples were dehydrated by heating to 500° C. (10° C. $min^{-1}$ ramp) under 16 and 4 mL $min^{-1}$ He and $O_2$, respectively, for 1 h before measurement. Solid-state $^{51}V$ MAS NMR spectra were acquired on an Avance NMR spectrometer (Bruker, Karlsruhe, Germany) operating at a 1H Larmor frequency of 400 MHz. The samples were spun around the magic angle with a rate of 18 kHz at room temperature using a double resonance 3.2 mm probe (containing ca. 15 mg sample). The probe was tuned to the resonance frequencies of 51V (105.246 MHz). The parts per million scale of the spectra was calibrated using the $^{13}C$ signal of adamantane as an external secondary reference. Samples were dehydrated under a flow of dry air at 500° C. for 3 h prior to the NMR measurements. Infrared spectra were recorded on a self-supporting wafer using a Bruker Alpha spectrometer in transmission mode (resolution of 2 $cm^{-1}$). The intensities were normalized to the Si—O—Si overtones of the silica framework. Diffuse reflectance UV-vis spectra were recorded with a Maya 200 spectrometer (Ocean Optics) equipped with a UV-vis deuterium/halogen light source (DH-2000-BAL from Mikropack) using $BaSO_4$ as a background. Both FT-IR and UV-vis analysis were carried out inside a glovebox (<1 ppm of $H_2O$ and $O_2$).

The point of zero charge (PZC) was determined according to a well-described method: titration of 0.1 M $HNO_3$ to a blank reference solution (3 mL 0.1 M $KNO_3$, 2 mL 0.01 M KOH, 5 mL DI $H_2O$) and reference solution plus conventional- (or pro-) $SiO_2$ gradually lowered the pH of the solution. Intersection of the titration curves of the blank solution with that of the solution plus conventional- (or pro-)$SiO_2$ indicated the pH at which the quantity of Si—$OH_2^+$ sites was equivalent to that of Si—$O^-$ sites, defined as the PZC. The titration curves are provided in the figures herein.

Vanadium loadings were determined using induced coupled plasma optical emission spectroscopy (ICP-OES) after complete acid digestion. Surface area and pore volume calculations were performed using Micromeritics 3-Flex instrumentation (t-plot analysis). Bulk analysis was repeated three times to accurately determine the metal oxide surface density.

ODHP Catalytic Activity. Catalytic activity measurements were performed using a Microactivity-Effi reactor. A total of 60-150 mg of catalyst (particle size of 600-710 μm) was mixed with inert SiC particles of equal size in a ratio of 2:1 (SiC-to-catalyst) and packed inside a quartz reactor tube (9 mm ID). Reactions were carried out at 490° C. with inlet flow ratios of 3:6:11 $O_2/C_3H_8/N_2$. Exhaust streams were analyzed using a Shimadzu 2010 GC equipped with three Restek columns (Rtx-1, Rt-Q-Bond, and RT-Msieve 5A) and a thermal conductivity detector (TCD) and flame ionization detector (FID). The catalysts were investigated under different contact times to monitor product selectivity at varying propane conversions (inverse weight-hour-space-velocity ($WHSV^{-1}$) of 20-140 [kg-cat s $m^{-3}$]). The carbon balance of each data point closes within 5%.

TABLE 2

Surface area and metal loadings of V, Na, Li, K, Rb and Mg of prepared catalysts on im-$SiO_2$ and pro-$SiO_2$.

| Impurity | ppm |
| --- | --- |
| Al | 937 |
| As | 26 |
| Ba | 10 |
| Ca | 636 |
| Cr | 3 |
| Fe | 151 |
| Mg | 81 |
| Na | 1649 |
| Ti | 92 |
| Total | 3585 |

TABLE 3

Impurity analysis of $SiO_2$ batch #MKBN2949V (im-$SiO_2$) provided by Sigma-Aldrich.

| $SiO_2$ type | Wt % V (%) | Surface area ($m^2\ g^{-1}$) | V $nm^{-2}$ | Wt % promoter (%) | Promoter species |
| --- | --- | --- | --- | --- | --- |
| im-$SiO_2$ | 1.75 ± 0.02 | 159 | 1.3 ± 0.2 | 0.4 | Na |
| | 4.32 ± 0.27 | 125 | 4.1 ± 0.3 | | |
| | 6.32 ± 0.33 | 104 | 7.2 ± 0.4 | | |
| | 7.18 ± 0.71 | 95 | 8.9 ± 0.9 | | |
| | 11.08 ± 0.70 | 98 | 13.4 ± 0.9 | | |
| | 12.29 ± 0.13 | 94 | 15.4 ± 0.5 | | |
| pro-$SiO_2$ | 6.03 ± 0.07 | 100 | 7.1 ± 0.5 | | |
| | 6.2 ± 0.11 | 85 | 8.6 ± 0.6 | | |
| | 6 | — | — | 0.1 | Li |
| | 6 | — | — | 0.2 | |
| | 6 | — | — | 0.4 | |
| | 6 | — | — | 0.2 | K |
| | 6 | — | — | 0.68 | |
| | 6 | — | — | 1 | |
| | 6 | — | — | 0.4 | Rb |
| | 6 | — | — | 2 | |
| | 6 | — | — | 3 | |
| | 6 | — | — | 0.2 | Mg |
| | 6 | — | — | 0.4 | |
| | 6 | — | — | 0.8 | |

Equations
Surface density, (M) $mn^{-2}$ $$\text{surf density} = \frac{\text{wt \%}\ M \times 6.02 \times 10^{23}}{MW_M \times \text{surf area} \times 10^{18}}$$

where $MW_M$=molecular weight of metal. M (g $mol^{-1}$)
wt % M=loading of metal, M (%)
surf area=surface area of catalyst ($m^2\ g^{-1}$)
Propylene selectivity, S $$S = \frac{F_{C3H6,out}}{\Sigma F_{carbon\ prod}}$$

where $F_{C3H6,out}$=flow of propylene out of reactor (mol $s^{-1}$ g-$cat^{-1}$)
$F_{carbon\ prod}$=flow of all carbon products out of reactor (mol $s^{-1}$ g-$cat^{-1}$)
Propane Conversion, X $$X = \frac{\Sigma F_{carbon\ prod}}{F_{C3H8,in}}$$

where $F_{carbon\ prod}$=flow of all carbon products out of reactor (mol $s^{-1}$ g-$cat^{-1}$)
$F_{C3H8,in}$=flow of propane into the reactor (mol $s^{-1}$ g-$cat^{-1}$)

From Serendipity to a Reproducible Synthesis Procedure. Use of impure $SiO_2$ (im-$SiO_2$) delivered directly from Sigma-Aldrich (batch #MKBN2949 V) allowed for a significantly better dispersion of vanadia than ever observed before. Indeed, $V_2O_5$ nanoparticles could not be detected up until a surface coverage as high as 8.9 V $nm^{-2}$ (see below). Systematic addition of the various metal impurities found in im-$SiO_2$ (determined by ICP-OES) to conventional $SiO_2$ via incipient wetness impregnation (see Experimental section) revealed $Na^+$ to be the responsible promoter. The enhanced dispersion properties of im-$SiO_2$ could be reproduced by adding 0.40 wt % $Na^+$ using a 1 M Na($NO_3$) solution via incipient wetness impregnation to conventional-$SiO_2$ to create Na+– promoted material (pro-$SiO_2$). Impregnation of vanadia to a $SiO_2$ support containing <0.40 wt % $Na^+$ did not show the enhanced dispersion effect (viz. formation of $V_2O_5$ particles), while impregnation of vanadia to $SiO_2$ material containing $Na^+$ loadings of ≥1.0 wt % revealed the formation of sodium metavanadate (FIG. 17).

Surprisingly, when substituting sodium with other alkali or alkaline earth metals ($Li^+$, $K^+$, $Rb^+$, $Mg^{2+}$) with comparable promoter/V molar ratios, no enhanced 2D vanadia dispersion could be observed. Indeed, Raman spectroscopy reveals the formation of 3D $V_2O_5$ in almost all prepared samples (FIG. 18). Catalysts containing higher amounts of promoter species show the emergence of unexpected Raman signals, distinct from that of supported V/SiO$_2$, likely due to the formation of a type of alkali-vanadate structure, similar to that detected for Nametavanadate. It appears that sodium ions have the optimal properties to facilitate this unique dispersion enhancement.

Previous studies explored alkali-metal promoters for supported vanadium catalysts to neutralize acidic sites on various supports, and investigated its effect on the redox behavior. It is worth emphasizing that in one study, the authors varied the molar ratio of Na/V between 0:1 and 1:1 for V/CeO$_2$ catalysts and monitored the effect on reducibility and activity for ODH of methanol. At Na/V ratios <0.25, sodium addition only marginally decreased redox ability and showed no negative effect on catalytic activity, while the opposite is true with Na/V ratios >0.25.

In this example, we focus on the effect of the Na$^+$-promoter on the structural properties of supported metal oxides on SiO$_2$ and couple this to the reactivity of the material using ODHP as a structure-sensitive probe reaction.

Enhancing 2D Dispersion.

Figure 11:
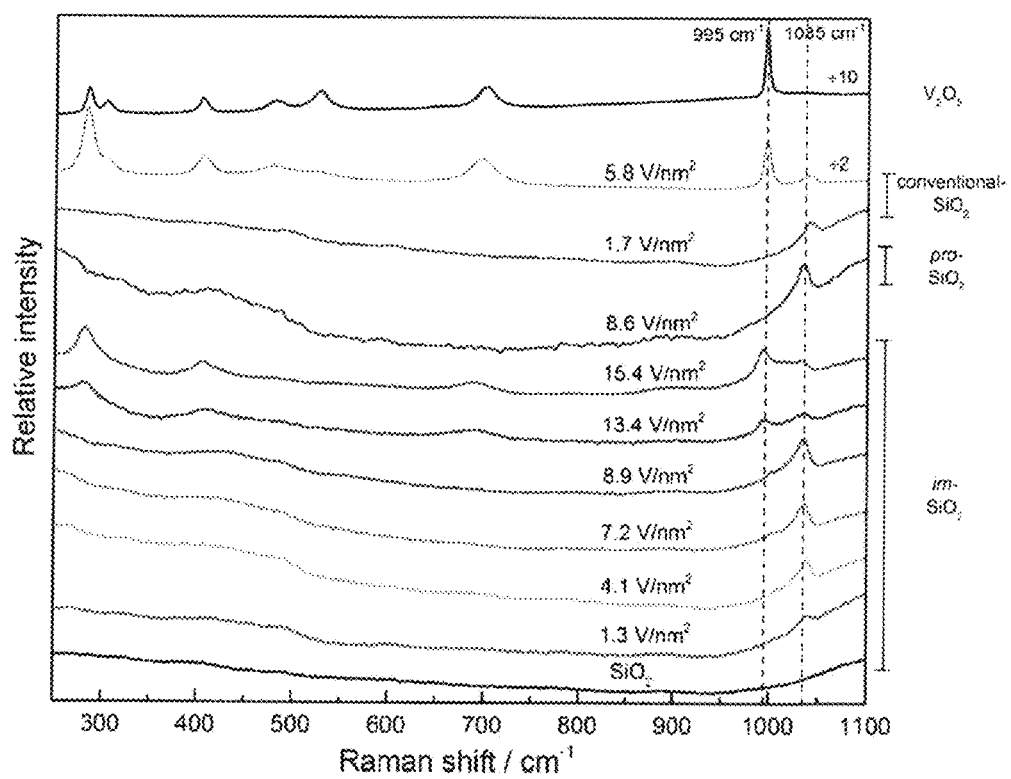
FIG. 11 shows Raman spectra of dehydrated vanadia catalysts supported on im-$SiO_2$, pro-$SiO_2$, and conventional-$SiO_2$, compared to the Raman spectra of im-$SiO_2$ (bottom) and bulk $V_2O_5$ (top). Materials showing Raman features at 995, 700, 500, 400, and 300 cm$^{-1}$ indicate the formation of $V_2O_5$ nanoparticles, while those only showing a band at 1035 cm$^{-1}$ indicate supported two-dimensional vanadia species.

Raman spectra of the prepared materials are displayed in FIG. 11. Under dehydrated conditions, each catalyst shows a Raman feature at 1035 cm$^{-1}$, assigned to V=O stretching of 2D vanadia species. In agreement with previous Raman studies of supported vanadia on silica, vanadia supported on conventional SiO$_2$ shows the emergence of 3D $V_2O_5$ particles above a modest surface density of 1.7 V nm$^{-2}$. This is indicated by the appearance of a sharp signal at 995 cm$^{-1}$, as well as more broad features at 700, 530, 500, 400, and 300 cm$^{-1}$. In the case of vanadia supported on im-SiO$_2$, these 3D $V_2O_5$ peaks do not appear at or below 8.9 V nm$^{-2}$, suggesting that a higher surface density of dispersed vanadia species can be obtained. With supported vanadia on pro-SiO$_2$, none of the 3D $V_2O_5$ peaks appear even with 8.6 V nm$^{-2}$. This result indicates that the enhanced dispersion properties of im-SiO$_2$ can be elegantly mimicked with the addition of 0.40 wt % Na$^+$ promoter.

It is important to note that the V=O stretching vibration of 2D vanadia at 1035 cm$^{-1}$ does not shift to lower wavenumbers upon the addition of Na$^+$. This suggests that the V=O bond does not weaken upon Na$^+$ promotion as was observed in earlier work for higher Na$^+$ loadings.

In addition to the Raman spectra, diffuse reflectance UV-vis (DRUV-vis) edge energy shifts of dehydrated vanadia catalysts supported on im-SiO$_2$ were determined (FIG. 19). The edge energies of supported vanadia materials is an indicator of the V$^{5+}$ ligand-to-metal charge transfer (LMCT) band, which shifts to lower energies with greater polymerization, due to greater electron delocalization in polymeric and 3D species. All catalysts identified to contain only 2D vanadia via Raman characterization show edge energies between 3.30 and 3.40 eV. Meanwhile, catalysts with the highest vanadia surface density (i.e., 13.4 and 15.4 V nm$^{-2}$), containing 3D vanadia species as shown by Raman analysis, are characterized by lower edge energies between 2.28 and 2.60 eV. The literature assigns edge energies between 3.30 and 3.40 eV to isolated monomeric vanadia, while edge energies of 2.28-2.60 eV correspond to 3D nanoparticles. Use of DRUV-vis edge energy analysis therefore corroborates our Raman spectroscopic assignments that 2D vanadia species can exist on Na$^+$-promoted SiO$_2$ up to 8.9 V nm$^{-2}$. No indication for polymeric species (edge energies around 3.0 eV) could be observed, in agreement with previous assertions that polymeric V—O—V species do not form on silica, in contrast to other supports.

Figure 12:
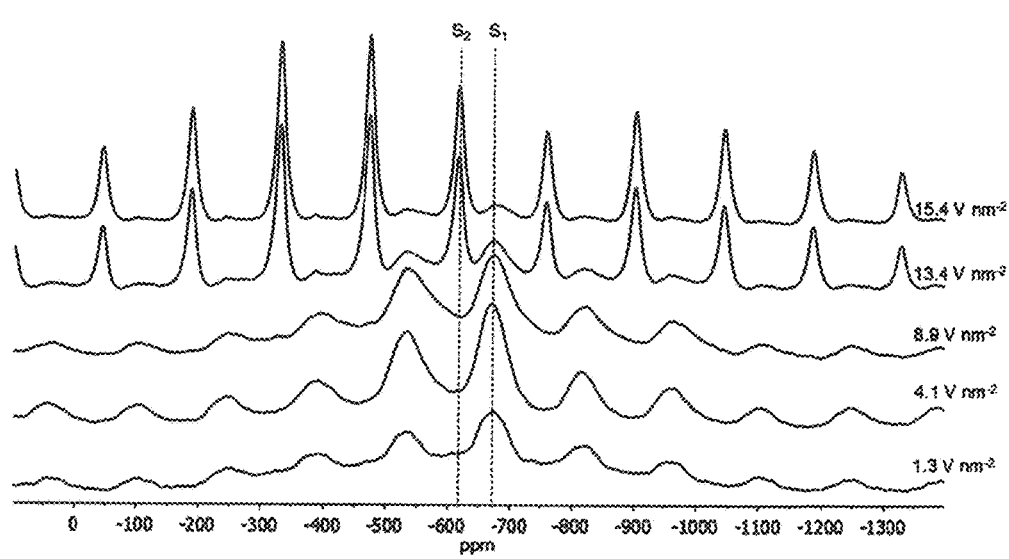
FIG. 12 shows $^{51}$V MAS NMR of dehydrated vanadia catalysts supported on im-$SiO_2$. Each catalyst shows an isotropic shift at −675 ppm ($S_1$), owing to the tetrahedral, monomeric vanadia species. Only catalysts above 8.9 V nm$^{-2}$ show an additional isotropic shift at −614 ppm ($S_2$), attributed to the presence of 3D $V_2O_5$.

Solid-state $^{51}$V MAS NMR spectra of dehydrated vanadia supported im-SiO$_2$ samples are displayed in FIG. 12. Two distinct isotropic shifts are observed, effectively separating catalysts with and without 3D $V_2O_5$ nanoparticles. Here, the signal at −675 ppm, featuring many spinning side-bands, is assigned to the dispersed, monomeric VO$_4$ species. The same isotropic shift appears in all investigated samples, regardless of the vanadia loading, suggesting the presence of analogous noninteracting species among these materials. The sharp signal appearing at −614 ppm is attributed to the distorted trigonal bipyramidal geometry of crystalline $V_2O_5$ and only appears for the samples containing the highest vanadia surface densities (i.e., 13.4 and 15.4 V nm$^{-2}$). This is in good agreement with previous works showing an isotropic shift of crystalline $V_2O_5$ at −612 ppm and −610 ppm. We emphasize that the $V_2O_5$ nanoparticles could not be detected with powder XRD, indicating that they must be very small in size. No NMR evidence could be found for the formation of oligomeric species, which is expected to show an isotropic shift at −350 ppm. This observation is in agreement with our DRUV-vis results discussed above. Interestingly, the isotropic shift of the isolated vanadia species (i.e., −675 ppm) is slightly shifted compared to a VO(OSiPh$_3$)$_3$ reference (i.e., −720 ppm) and compared to dispersed vanadia on unpromoted silica (viz., −694 ppm, see FIG. 20). This slight deshielding could point toward a weak (long distance) interaction of the vanadia with the sodium promotor.

The enhanced dispersion when using im-SiO$_2$ is not exclusive to supported vanadia but is also observed with the other group V metal oxides (i.e., niobium and tantalum oxides; see Raman spectra in FIG. 21). Using conventional SiO$_2$, the maximum reported surface densities of supported Nb and Ta oxides were 1.1 Nb nm$^{-2}$ and 0.8 Ta nm$^{-2}$, respectively. When supported on im-SiO$_2$, these limits are expanded to at least 2.5 Nb nm$^{-2}$ and 2.9 Ta nm$^{-2}$ as the corresponding materials do not show Raman features of their respective 3D metal oxide species.

Catalytic Activity.

Figure 13:
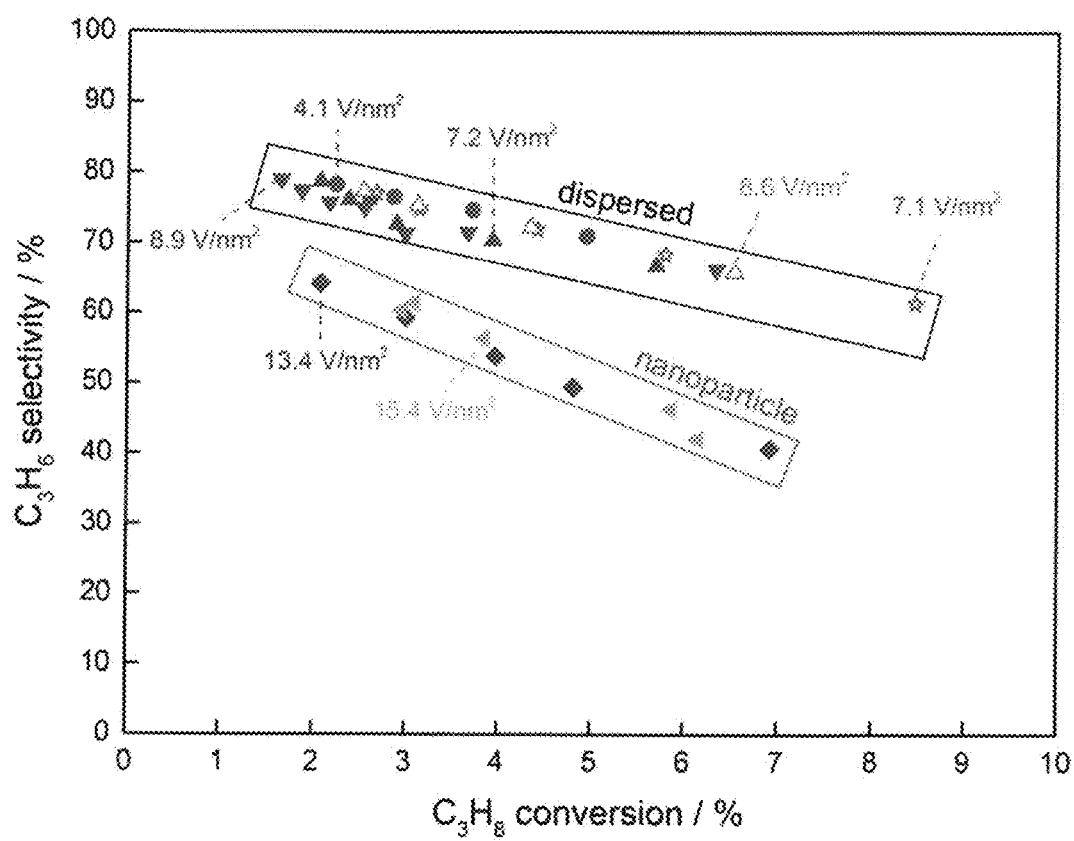
FIG. 13 shows propylene selectivity plotted as a function of propane conversion for vanadia catalysts supported on im- and pro-$SiO_2$. Catalysts containing $V_2O_5$ nanoparticles (vide supra) show a noticeable decrease in propylene selectivity compared to catalysts containing only 2D dispersed vanadia. Open symbols indicate pro-$SiO_2$ support material, while all others use im-$SiO_2$.

The strong structure-sensitivity of ODHP can be conveniently used to characterize supported vanadium materials. When plotting the propylene selectivity as a function of propane conversion for the various catalysts (FIG. 13), two different types of catalysts can be distinguished. Indeed, the materials featuring $V_2O_5$ nanoparticles show an overall lower selectivity and a more rapid decrease of the selectivity as a function of conversion, pointing toward enhanced propylene combustion, in line with the literature data.

Figure 14:
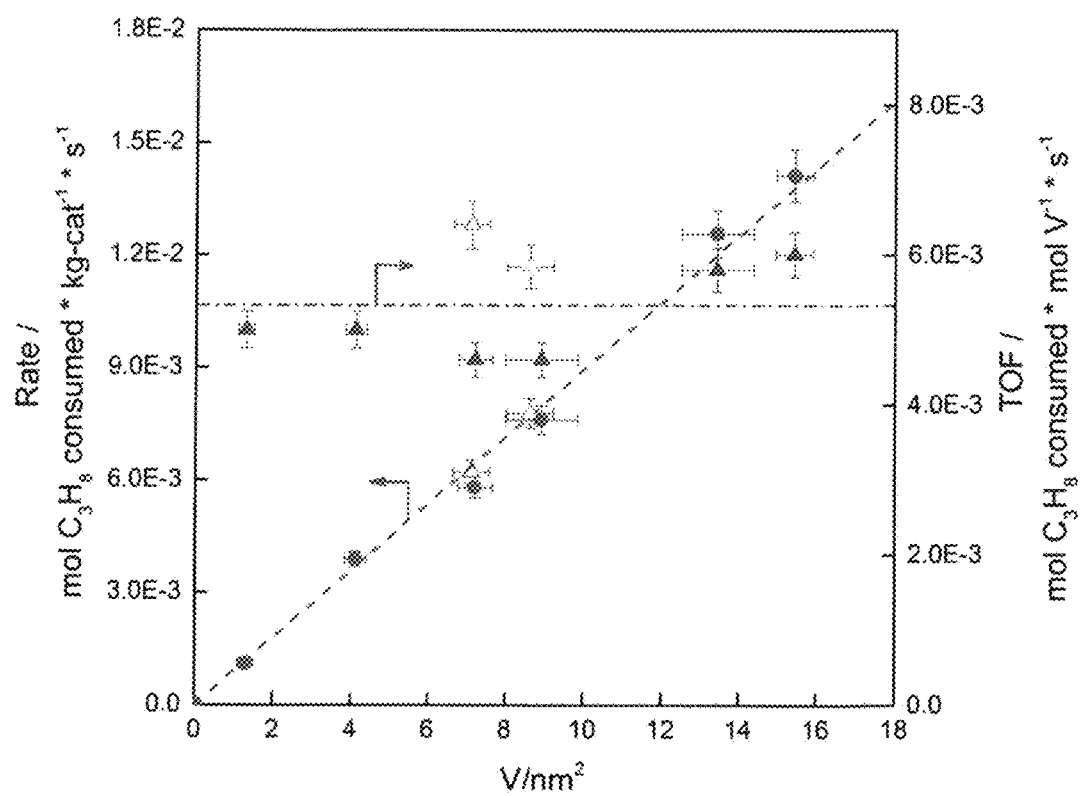
FIG. 14 shows the rate of propane consumption (left-axis, blue data points) and TOF (right-axis, red data points)

In FIG. 14, we show that the propane consumption rate is proportional to the vanadium surface density. We emphasize that the TOF, as well as the apparent activation energy of the submonolayer materials, is independent of the vanadium loading and in line with the reported data for V/SiO$_2$, i.e. $(5.3\pm0.7)\times10^{-3}$ s$^{-1}$ and 116±6 kJ mol$^{-1}$, respectively. Coupled with the results in FIG. 13, this indicates that the higher dispersion of vanadium results in a higher space-time yield, while not affecting the propylene selectivity. Previous work reported that alkali promoters significantly reduce the propane consumption TOF. This effect is not noticed here when promoting SiO$_2$ with only 0.40 wt % Na$^+$ and is likely due to the low molar ratios of Na$^+$ to vanadium used in these pro-SiO$_2$ materials (<0.25 Na/V) compared to previous works (>1:1 Na/V). Also based on the 51 V-NMR results discussed above, it appears that the low amount of sodium does not significantly affect the molecular environment of the vanadia sites, only showing a minor deshielding of the vanadium by the sodium. This hypothesis is also in line with our observation that the catalytic activity of 5.6 wt % V supported on $SiO_2$ containing 2.2 wt % $Na^+$ (~1:1 Na:V) shows a 40% decrease in TOF (viz., $3.1 \times 10^{-3}$ s$^{-1}$) and is also associated with a lower propylene selectivity than that of 2D vanadia supported on pro-$SiO_2$ or im-$SiO_2$ (see FIG. 22). The rate of propane consumption remains proportional to vanadium surface density, even with the emergence of 3D $V_2O_5$ above 9 V nm$^{-2}$. Considering this result, as well as the noticeable drop in selectivity upon formation of 3D $V_2O_5$ (FIG. 13), the existence of 3D $V_2O_5$ appears to increase the rate of consecutive propylene combustion to COx.

Catalysts with high vanadia surface density remain stable for at least 4.5 days on stream, despite the high temperature and the formation of water as a reaction product. This is illustrated in FIG. 15 for the case of 2D vanadia on pro-$SiO_2$ (8.6 V nm$^{-2}$), maintaining a stable propylene selectivity (66%) at 6.5% propane conversion. The spent catalyst was characterized using Raman to verify the absence of structural changes during the reaction. Neither Raman bands of 3D $V_2O_5$ nor those corresponding to coke deposition could be observed (FIG. 23).

Hypothesis for the Potential Role of Sodium as a Promoter.

Metal oxide nanoparticles are formed when it becomes more favorable to anchor to supported metal oxide species rather than support-oxide anchoring sites during the impregnation and/or calcination. As a working hypothesis, we propose that Na+ enhances 2D metal oxide dispersion on $SiO_2$ by exchanging with surface silanol groups, making these anchoring sites more reactive. This hypothesis is supported by IR spectroscopy (FIG. 24), comparing spectra of dehydrated conventional-$SiO_2$ to pro-$SiO_2$. Sodium addition reduces the amount of silanol groups (features between 3745 and 3660 cm$^{-1}$) upon formation of more nucleophilic SiO— species. This observation is also in line with the shift in the point of zero charge (PZC) from a pH of 4.4 to 6.3 upon the addition of sodium to Aerosil200 (FIG. 25).

The highly nucleophilic ≡SiONa sites can more readily react with the VO(O$^i$Pr)$_3$ precursor, yielding a surface bound ≡SiO—V(O)(O$^i$Pr)$_2$ species plus NaO$^i$Pr. The basic sodium isopropoxide could react with a less reactive silanol group, regenerating the more favorable ≡SiONa anchoring site. Our proposed (catalytic) mechanism for Na$^+$-assisted vanadiumoxide anchoring is displayed in Scheme 1. We envision that this mechanism could help in preferential multipodal bonding of the vanadium to the silica surface rather than atop surfacebound vanadium sites.

This proposed mechanism could also explain the necessity for an optimal amount of sodium to be present to observe enhanced 2D dispersion. It is indeed plausible that each silanol activating This proposed mechanism could also explain the necessity for an optimal amount of sodium to be present to observe enhanced 2D dispersion. It is indeed plausible that each silanol activating silanol activating Na$^+$ species can only migrate a limited distance before becoming surrounded by anchored vanadia species. No longer able to migrate via the proposed ion-exchange mechanism, vanadium-surrounded Na$^+$ species cannot activate the remaining unreactive silanol groups, leaving any unanchored VO(O-$^i$Pr)$_3$ precursor to anchor to already surface-bound vanadia during the calcination step, thus forming 3D $V_2O_5$. No evidence for the formation of VONa bonds could be found in the calcined materials, and $^{51}$V NMR indicates only a slight downfield shift of the (SiO)$_3$V≡O vanadia centers upon the addition of sodium. Attempts to capture this effect using $^{23}$Na MAS NMR with pro-$SiO_2$ catalysts have been unsuccessful to date due to the low signal-to-noise ratio, likely caused by (1) the low sodium content and, more importantly, (2) the amorphous nature of the support leading to peak broadening. The proposed hypothesis will be further investigated, also to explore why it is that other alkali and alkali-Earth metal ions (Li$^+$, K$^+$, Rb$^+$, Mg$^{2+}$) do not display the same enhanced 2D dispersion effect that Na+-promoted $SiO_2$ offers. Most likely, sodium ions present an optimal balance between charge density and solvation by the isopropanol solvent used during the impregnation.

Structural properties of supported metal oxides, particularly the presence of 2D or 3D metal oxide species, control their catalytic performance. Out of all traditional oxide supports, $SiO_2$ has historically allowed the lowest 2D metal oxide dispersion, despite its high surface area. Using Raman and DRUV-vis spectroscopy, $^{51}$V-NMR, and catalytic activity data with ODHP as a probe reaction, we now show that the promotion of conventional silica with 0.40 wt % Na$^+$ can significantly enhance the dispersion of vanadia on $SiO_2$ to levels equivalent to that of other common oxide supports (i.e., up to 8.9 V nm$^{-2}$). Increasing the quantity of 2D vanadia serves to proportionally increase the rate of propane ODH while maintaining high propylene selectivity. Raman spectroscopy further confirms enhanced dispersion of the other group V metal oxides (Nb, Ta oxide) on Na$^+$-promoted $SiO_2$. It is hypothesized that the role of Na$^+$ is to ion-exchange with surface silanols to form more-reactive Si—O—Na$^+$ anchoring sites. The silanol groups that would normally remain unreactive toward the metal oxide precursor now have the ability to function as an anchoring site. From the optimal Na/V ratio of 0.2, and the fact that the sodium promotion nearly triples the amount of dispersed vanadia, we propose a catalytic mechanism in which one sodium ion is able to facilitate the anchoring of several vanadia species. The enhanced metal oxide dispersion effect is displayed here for the case of group V metal oxides but likely includes other metal oxides as well. This finding presents exciting new opportunities for metal oxide catalysts supported on $SiO_2$.

References in Example 3

1. Hu, J.; Chen. L.; Richards, R. In Metal Oxide Catalysis; Jackson, S. D., Hargreaves, J. S. J., Eds.; Wiley-VCH Verlag GmbH & Co. KGaA: Weinheim, Germany, 2009; pp 613-661.
2. Chatzidimitriou, A.; Bond, J. Q. Green Chem. 2015, 17, 4367-4376.
3. Tian, H.; Ross, E. I.; Wachs, I. E. J. Phys. Chem. B 2006, 110, 9593-9600.
4. Russell. A.; Stokes, J. Ind. Eng. Chem. 1946, 38, 1071-1074.
5. Ren, T.; Patel, M.; Blok, K. Energy 2006, 31, 425-451.
6. Cavani, F.; Ballarini, N.; Cericola, A. Catal. Today 2007, 127, 113-131.
7. Pless. J.; Bardin, B.: Kim, H.; Ko, D.; Smith. M. T.; Haammond, R. R.; Stair, P. C.; Poeppelmcier. K. R. J. Catal. 2004, 223, 419-431.
8. Zhao, Z.; Gao, X.; Wachs, I. E. J. Phys. Chem. B 2003, 107, 6333-6342.
9. Yuan, L.; Bhatt, S.; Beaucage, G.; Guliants, V. V.; Mamedov, S.; Soman, R. S. J. Phys. Chem. B 2005, 109, 23250-23254.
10. Zhai, Z.; Wang, X.; Licht, R.; Bell, A. T. J. Catal. 2015, 325, 87-100.

11. Vajda, S.; Pellin, M. J.; Greeley, J. P.; Marshall, C. L.; Curtiss, L. A.; Ballentine, B. A.; Elam, J. W.; Catillon-Mucherie, C.; Redfern, P. C.; Mehmood, F.; Zapol, P. Nat. Mater. 2009, 8, 213-216.
12. Frank, B.; Zhang, J.; Blume, R.; Schlogl, R.; Su, D. S. Angew. Chem., Int. Ed. 2009, 48, 6913-6917.
13. Sui, Z. J.: Zhou, J. H.; Dai, Y. C.; Yuan, W. K. Catal. Today 2005, 106, 90-94.
14. Schwarz, O.; Habel, D.; Ovsitser, O.; Kondratenko, E. V.; Hess, C.; Schomacker, R.; Schubert, H. J. Mol. Catal. A: Chem. 2008, 293, 45-52.
15. Carrero, C. A.; Keturakis, C.; Orrego, A.; Schomaeker, R.; Wachs, I. E. Dalton Trans. 2013, 42, 12644-12653.
16. Kondratenko, E. V.; Cherian, M.; Baerns, M. Catal. Today 2006, 112, 60-63.
17. Kondratenko, E. V.: Cherian, M.; Baerns, M.; Schloegl, R.; Wang, X.; Wachs. I. E.; Su, D. J. Catal. 2005, 234, 131-142.
18. Testova, N. V.; Shalygin, A. S.; Kaichev, V. V.; Glazneva, T. S.; Paukshtis, E. A.; Parmon, V. N.; Appl. Catal., A, 2015, http://dx.doi.org/10.1016/j.apcata.2015.05.018. DOI: 10.1016/j.apcata.2015.05.018.
19. Takehira, K.; Ohishi, Y.; Shishido, T.; Kawabata, T.; Takaki, K.; Zhang, Q.; Wang, Y. J. Catal. 2004, 224, 404-416.
20. Shishido, T.; Shimamura, K.; Teramura, K.; Tanaka, T. Catal. Today 2012, 185, 151-156.
21. Chen, K.; Bell, A. T.; Iglesia, E. J. Phys. Chem. B 2000, 104, 1292-1299.
22. Argyle, M. D.; Chen, K.; Bell, A. T.; Iglesia, E. J. Catal. 2002, 208, 139-149.
23. Malleswara Rao, T. V.; Deo, G. AIChE J. 2007, 53, 1538-1549.
24. Dinse, A.; Frank, B.; Hess, C.; Habel, D.; Schomaeker, R. J. Mol. Catal. A: Chem. 2008, 289, 28-37.
25. Grabowski, R. Appl. Catal., A 2004, 270, 37-47.
26. Schwarz, O.; Duong, P.; Schaefer, G.; Schomaeker, R. Chem. Eng. J. 2009, 145, 420-428.
27. Frank, B.; Dinse, A.; Ovsitser, O.; Kondratenko, E. V.; Schomaeker, R. Appl. Catal., A 2007, 323, 66-76.
28. Rozanska, X.; Fortrie, R.; Sauer, J. J. Am. Chem. Soc. 2014, 136, 7751-7761.
29. Dai, G. L.; Li, Z. H.; Lu, J.; Wang, W. N.; Fan, K. N. J. Phys. Chem. C 2012, 116, 807-817.
30. Rozanska, X.; Fortrie, R.; Sauer, J. J. Phys. Chem. C 2007, 111, 6041-6050.
31. Alexopoulos, K.; Reyniers, M. F.; Marin, G. J. Catal. 2012, 289, 127-139.
32. Hofmann, A.; Ganduglia-Pirovano, M. V.; Sauer, J. J. Phys. Chem. C 2009, 113, 18191-18203.
33. Popa, C.; Ganduglia-Pirovano, M. V.; Sauer, J. J. Phys. Chem. C 2011, 115, 7399-7410.
34. Schimmoeller, B.; Jiang, Y.; Pratsinis, S. E.; Baiker, A. J. Catal. 2010, 274, 64-75.
35. Carrero, C. A.; Schloegl, R.; Wachs, I. E.; Schomaecker, R. ACS Catal. 2014, 4, 3357-3380.
36. Gao, X.; Bare, S. R.; Weckhuyscn, B. M.; Wachs, I. E. J. Phys. Chem. B 1998, 102, 10842-10852.
37. Wachs, I. E. Catal. Today 1996, 27, 437-455.
38. Wang, X.; Wachs, I. E. Catal. Today 2004, 96, 211-222.
39. Buyevskaya, O.; Bruckner, A.; Kondratenko, E.; Wolf, D.; Baerns, M. Catal. Today 2001, 67, 369-378.
40. Bourikas, K.; Vakros, J.; Kordulis, C.; Lycourghiotis, A. J. Phys. Chem. B 2003, 107, 9441-9451.
41. Lemonidou, A. A.; Nalbandian, L.; Vasalos, I. Catal. Today 2000, 61, 333-341.
42. Garcia Cortez, G.; Fierro, J. L. G.; Banares, M. A. Catal. Today 2003, 78, 219-228.
43. Li, Y.; Wei, Z.; Sun, J.; Gao, F.; Peden, C. H. F.; Wang, Y. J. Phys. Chem. C 2013, 117, 5722-5729.
44. Lee, E. L.; Wachs, I. E. J. Phys. Chem. C 2007, 111, 14410-1442.
45. Wu, Z.; Kim, H. S.; Stair, P. C. In Metal Oxide Catalysis; Jackson, S. D., Hargreaves, J. S. J., Eds.; Wiley-VCH Verlag GmbH & Co. KGaA: Weinheim, Germany, 2009; pp 177-194.
46. Feher. F. J.; Blanski, R. L. J. Am. Chem. Soc. 1992, 114, 5886-5887.
47. McGregor, J. In Metal Oxide Catalysis; Jackson, S. D., Hargreaves, J. S. J., Eds.; Wiley-VCH Verlag GmbH & Co. KGaA: Weinheim, Germany, 2009; pp 195-242.
48. Hu, J. Z.; Xu, S.; Li, W.; Hlu, M. Y.; Deng, X.; Dixon, D. A.; Vasiliu, M.; Craciun, R; Wang, Y.; Bao, X.; Peden, C. H. F. ACS Catal. 2015, 5, 3945-3952.

Example 4: Improved Supported Metal Oxides for the Oxidative DeHydrogenation of Propane The oxidative dehydrogenation of propane (ODHP) is a highly attractive reaction for the on-purpose production of propylene. Unfortunately, rapid consecutive over-oxidation of the desired olefin limits the selectivity and hampers the industrial feasibility. Supported metal oxides, and in particular dispersed vanadium containing materials, have shown promising results. Yet one has to improve both the selectivity and activity (space-time-yield) to make this reaction economically attractive. In this contribution we build upon our previous work that allowed us to increase the dispersion of group V metal oxides on silica to prepare a ternary metal oxide catalyst based on vanadium and tantalum that shows superior selectivity and productivity.

Introduction

The great abundance of shale gas has initiated a renaissance in the chemical industry [1]. One of the effects is a shift from naphtha to ethane cracking at the heart of the chemical value chain. As a consequence, the United States is now one of the low cost producers of ethylene. Indeed, the ethylene production costs dropped from close to $0.6/pound in 2005 to below $0.3/pounds currently, causing an expected growth in the production of polyethylene by more than 50% by 2020 [2]. However, this feedstock shift also brings about challenges for the production of other olefins, in particular propylene. As an example, steam cracking of naphtha typically produces 31% ethane, 16% propylene and 8% crude C4s (plus pyrolysis gasoline and hydrogen). With ethane as a feedstock, steam cracking produces close to 80% ethylene but only 3% propylene and 3% crude C4s. As a consequence, the demand for propylene is growing far more rapidly than can be satisfied by steam cracking (FIG. 26) [3]. It is expected that the propylene demand will increase from about 100 to 120 million MTA by 2020, while it is estimated that steam cracking will only be able to produce 60 million MTA by 2020, i.e. half the demand.

One of the already implemented technologies to fill the demand gap is DeHydrogenation (DH) of propane (equation 1), obtained from the "wet fraction" of shale/natural gas. The three most important DH technologies are: (1) Oleflex (UOP), (2) Catofin (Lummus), and (3) STAR (Uhde) [4]. In order to drive this endothermic reaction ($\Delta H°_{298}$=+124 kJ mol-1), high reaction temperatures are required (550-750° C.), causing rapid catalyst deactivation due to coking. Various technological solutions have been engineered to handle this problem, such as Continuous Catalyst Regeneration (CCR by UOP), or the use of parallel fixed bed reactors that alternate between catalyst regeneration and on-stream operation (e.g. Catofin process).

$$C_3H_8 \rightarrow C_3H_6 + H_2 \quad (1)$$

The endothermicity of this process makes this technology rather energy intensive. Co-feeding of oxygen and propane could result in the Oxidative DeHydrogenation of propane (ODHP), making the reaction exothermic ($\Delta H°_{298}$=−117 kJ mol$^{-1}$) and prevents the formation of carbon deposition. Unfortunately this approach leads to problems of rapid consecutive over-oxidation, a general problem for partial oxidations [5].

A widely investigated class of catalysts for ODHP are supported vanadium oxide materials [6-16]. Strong structure-dependent performance has been reported: the presence of site-isolated, or highly dispersed, vanadia species was shown to be key to obtain high selectivity [6]. The presence of $V_2O_5$ nanoparticles results in the acceleration of the undesired propylene combustion. Even for well-dispersed systems, it is well established that the support plays an important role in controlling the activity and selectivity [6]. For instance, $V/TiO_2$ materials are more active but also less selective than $V/SiO_2$. Aiming for synergetic effects, Schlögl and coworkers prepared a V/Ti/SBA-15 material [17]. This system indeed showed an enhancement of the catalyst's productivity (kg-$C_3H_6$ kg-cat$^{-1}$ hr$^{-1}$) by a factor of ~7, compared to a V/SBA-15 catalyst. While the V/Ti/SBA-15 catalyst shows enhanced productivity, its selectivity to propylene remains equivalent to (or slightly below) that of V/SBA-15. Thus, catalysts showing superior selectivity under ODH conditions are still highly sought after.

Recently, our group reported on a method to enhance the two-dimensional dispersion of Group V metal oxides on silica by promoting the support with small amounts of sodium [18]. Grant J T, et al. (2015) ACS Catal 5:5787-5793 is incorporated herein by reference in its entirety. This allowed us to increase the monolayer coverage from ~3 V nm$^{-2}$ to ~9 V nm$^{-2}$, avoiding the formation of $V_2O_5$ nanoparticles. In the present contribution we aim to investigate this system in more detail and use this technique to add an additional metal oxide to enhance the performance of the vanadium at high surface coverage.

Experimental

Material synthesis Sodium-promoted $SiO_2$ (pro-$SiO_2$) was prepared by incipient wetness impregnation (IWI) of a 1M $NaNO_3$ solution to conventional amorphous silica (Aerosil200 from Evonik; 200 m$^2$ g$^{-1}$). An appropriate amount of 1M $NaNO_3$ solution was diluted in deionized $H_2O$ to roughly equal the pore volume of Aerosil200 (1.3 mL g$^{-1}$). The Na-impregnated sample was then calcined under air, ramping 1.5° C. min$^{-1}$ to 700° C., holding at 700° C. for 4 h. Sodium loading of pro-$SiO_2$ is equal to 0.4 wt % Na$^+$.

All supported vanadium-oxide and tantalum-oxide catalysts were synthesized using IWI inside a glovebox under a dry N2 atmosphere. All samples were dried overnight in static conditions at 120° C. prior to metal impregnation. Metal alkoxide solutions were used as precursors, as these were previously shown to be superior to other precursors [8]. Supported vanadium oxide catalysts were synthesized by IWI of vanadium oxytriisopropoxide (VTI; Sigma-Aldrich) diluted in dry isopropanol (Sigma-Aldrich, 99.5%) onto pro-$SiO_2$. The ratio of vanadium-to-isopropanol was altered to create a variety of vanadium oxide loadings. Impregnated samples were vacuum-dried inside the glovebox and transferred to a calcination oven where they were dried under a flow of $N_2$ at 120° C. for 3 h, ramped to 550° C. at 1° C. min$^{-1}$ under dry air, and calcined at 550° C. for 3 h. Only a minor (i.e. 10%) decrease in specific surface area could be observed.

The ternary catalyst 4V/18Ta/pro-$SiO_2$ was prepared in a two steps procedure. An initial IWI treatment of tantalum ethoxide (Sigma-Aldrich, 99.98%) diluted in dry ethanol (Sigma-Aldrich, 99.5%) was made to pro-$SiO_2$. The tantalum-to-ethanol ratio was adjusted to create a final tantalum metal loading of 18 wt %. This sample was vacuum-dried inside the glovebox and transferred to a calcination oven to undergo the calcination procedure detailed above for supported vanadium oxide catalysts. The 18Ta/pro-$SiO_2$ catalyst was then dried overnight at 120° C. before transferring to a glovebox to undergo impregnation of VTI to allow for a vanadium loading of 4 wt % followed by vacuum-dry and calcination.

Characterization

Raman characterization was performed using a Renishaw InVia Raman Spectrometer using a 785 nm excitation laser. The analysis was done in a high-temperature Linkam CCR1000 cell. Samples were dehydrated by ramping 10° C. min$^{-1}$ and holding at 500° C. under 20 mL min$^{-1}$ of a 80% He, 20% $O_2$ gas mixture for 1 h before measurement. All measurements used a 1200 L mm$^{-1}$ grating and were taken with a range of 250-1100 cm$^{-1}$ and a dispersion of 1.36565 cm$^{-1}$ pixel$^{-1}$.

Solid-state $^{51}$V-NMR spectra were acquired on an Avance NMR spectrometer (Bruker) operating at a $^1$H Larmor frequency of 400 MHz. The samples were spun around the Magic Angle with a rate of 18 kHz at room temperature using a double resonance 3.2 mm probe (containing ca. 15 mg sample). The probe was tuned to the resonance frequencies of $^{13}$C (176.06 MHz). The ppm scale of the spectra was calibrated using the $^{13}$C signal of adamantane as an external secondary reference.

Diffuse Reflectance UV-Vis spectra were measured using a Maya 200 spectrometer (Ocean Optics) equipped with a UV-vis deuterium/halogen light source (DH-2000-BAL from Mikropack) using $BaSO_4$ as a background matrix. All measurements were recorded inside a glove box (<1 ppm $H_2O$ and $O_2$). Infrared spectra were measured on a self-supporting wafer using a Bruker Alpha spectrometer in transmission mode (resolution of 2 cm$^{-1}$). The intensities were normalized to the Si—O—Si overtones of the silica framework.

Metal loadings were determined using induced coupled plasma optical emission spectroscopy (ICP-OES) after complete acid digestion. Pore volumes and surface areas were performed using Micromeritics 3-Flex instrumentation (t-plot analysis).

Catalytic Testing

Catalytic measurement was performed using a Microactivity-Effi reactor. Reactions were carried out at 490° C. and ambient pressure with inlet flow ratios of 15% $O_2$ and 30% $C_3H_8$ (balance $N_2$). Total inlet flowrate was varied between 40-160 mL min$^{-1}$ to monitor product selectivity at varying propylene yields. The reactor bed contained 40-150 mg of catalyst particles (size 600-710 μm) diluted with inert SiC particles to ensure uniform catalyst bed temperature. These particles were packed inside a quartz reactor tube (9 mm ID). We carefully verified that there was negligible thermal background reactivity occurring under our experimental conditions (viz, homogeneous gas phase chemistry). Exhaust streams were analyzed using a Shimadzu 2010 GC equipped with three Restek columns (RTX-1, RT-Q-Bond, and RT-Msieve 5A), a flame ionization detector (FID) and a thermal conductivity detector (TCD). The carbon balance of each data point closes within ±5%.

Results and Discussion

Evidence for the Enhanced 2D Dispersion at Optimal Na/V Ratio

Diffuse Reflectance UV-Vis (DRUV-Vis) spectroscopy is widely used to conveniently differentiate between monomeric, polymeric and nanoparticles of vanadium oxide at the surface of catalytic materials [19]. The spectra in FIG. 27 illustrates that for V/pro-SiO$_2$ materials containing up to 7.2 wt % V (corresponding to 8.9 V nm$^{-2}$), no edge energies below 3.3 eV could be observed, indicating the exclusive presence of highly dispersed vanadia species. A slight increase in surface coverage immediately results in the formation of V$_2$O$_5$ particles, without the intermediate formation of polymeric species. This is in agreement with the literature hypothesis that one is not able to stabilize oligo-/polymeric species on SiO$_2$, unlike on other supports [19-21].

We emphasize that these unprecedented vanadium dispersion levels (up to ~9 V nm$^{-2}$) were only obtained when the amorphous silica support was promoted with 0.4 wt % of sodium (FIG. 28). Indeed, at lower sodium concentrations, we observed the undesired formation of V$_2$O$_5$ (keeping the vanadium content constant at 6 wt %). At higher sodium loading, we observed the formation of sodium metavanadate. Both V$_2$O$_5$ and sodium metavanadate are detrimental for the selectivity of the propane ODH reaction and should hence be avoided. It appears that an atomic ratio of ~8:1 V:Na (at monolayer coverage) is optimal to obtain the desired effect.

As previously reported [18], the enhanced 2D metal oxide dispersion afforded by pro-SiO$_2$ is not exclusive to supported vanadia but applies to the other Group V metal oxides as well, e.g. supported Nb-oxide and Ta-oxide. Raman spectroscopy was used to show that use of pro-SiO$_2$ as a support could increase the maximum supported 2D Nb-oxide and Ta-oxide species to at least 5.5 wt % Nb and 18 wt % Ta. We now show, for the case of the 4V/18Ta/pro-SiO$_2$ material (containing 4 wt % V and 18 wt % Ta), that also combinations of Group V metals can be anchored together on a surface, allowing for enhanced 2D dispersion of multiple metal oxides. Indeed, no Raman bands associated with 3D V$_2$O$_5$ or Ta$_2$O$_5$ nanoparticles are detected for the 4V/18Ta/pro-SiO$_2$ catalyst (FIG. 29).

Working Hypothesis Behind the Enhanced Dispersion

The addition of sodium was found to reduce both the isolated SiOH stretching vibrations (appearing at 3745 cm$^{-1}$) and H-bonded silanol groups (broad signal at 3660 cm$^{-1}$; see FIG. 30) by ~30%. In other words, the surface becomes less acidic, in line with the observed shift in the Point-of-Zero-Charge from pH 4.4 to 6.3 upon inclusion of the sodium promoter [18]. When we couple this observation with the literature hypothesis that vanadium dispersion on silica is limited due to the low reactivity of the surface silanol groups, this result suggests that the sodium forms ≡SiONa groups on the silica surface that are more reactive (nucleophilic) towards the vanadium oxytriisopropoxide precursor. The sodium isopropoxide that is formed in this anchoring reaction is a strong base that will readily react with a weakly acidic ≡SiOH group, regenerating the ≡SiONa groups. This proposed mechanism hence suggests that sodium plays a catalytic role in facilitating the anchoring of vanadium to the kinetically less reactive silica surface. It is the competition between the surface anchoring and the undesired formation of 3D V—O—V bonds that controls the final state of the material. This proposed mechanism can also explain why an optimal amount of sodium is necessary to observe enhanced 2D dispersion. The formed sodium isopropoxide may only be able to migrate a limited distance before becoming surrounded by anchored vanadia species. With too little Na$^+$-promoter available for silanol site activation and migration, it is possible that some available ≡SiOH groups remain unreactive, leaving the unanchored vanadium precursor to anchor to already surface-bound vanadia sites to form 3D V$_2$O$_5$.

Insights from Solid State $^{51}$V NMR

FIG. 31 compares the $^{51}$V MAS NMR spectra of various V/pro-SiO$_2$ samples with the spectra of a reference V/SiO$_2$ sample. All of the spectra show a single isotropic shift (highlighted in gray) with intense spinning side bands, indicating anisotropy. For surface-supported species, this corresponds to a less dynamic environment around the nucleus, meaning that the vanadium species are most likely multipodal (Si—O)$_3$=V=O species, preventing free rotation about their surface Si—O—V linkages. We emphasize that the observed line broadening for these $^{51}$V NMR spectra is predominantly caused by the amorphous nature of the silica support.

The absence of a sharp isotropic shift at −614 ppm in the V/pro-SiO$_2$ $^{51}$V MAS spectra up to vanadia coverages of 8.9 V nm$^{-2}$ (corresponding to 7.2 wt % V) confirms the absence of V$_2$O$_5$ particles [22,23]. The isotropic shift for V/SiO$_2$ is at −695 ppm, whereas the isotropic shift for all of the dispersed V/pro-SiO$_2$ samples is at −675 ppm. The subtle deshielding of the vanadium when the support is sodium-promoted points towards a slightly lower electron density at the vanadium nucleus. This could in principle cause an increase in the V=O bond strength, which is however not observed with Raman spectroscopy. Indeed, we observe a slightly lower V=O stretching frequency for the sodium-promoted material (viz. 1035 versus 1043 cm$^{-1}$). Based on these observations, we hypothesize that sodium could be interacting with the vanadyl oxygen atom (FIG. 32), causing a net weakening the V=O bond, while at the same time making the vanadium nucleus slightly more positive.

The $^{51}$V MAS NMR spectrum for the ternary V/Ta/pro-SiO$_2$ system shows a single isotropic shift at −685 ppm. It appears to experience the same subtle deshielding of the $^{51}$V nuclei compared to the V/SiO$_2$ system, although not to the same extent as the V/pro-SiO$_2$ materials. More importantly, this result indicates that the vanadium is still bound to the silica and not on top of the tantalum.

Catalytic ODHP Results

Catalysts with vanadium loadings above and below monolayer coverage were tested for differences in propylene selectivity and yield. All catalysts containing less than 7.2 wt % V (corresponding to 8.9 V nm$^{-2}$) supported on pro-SiO$_2$ show higher selectivity to propylene than those with higher vanadium loadings at comparable propylene yields (see FIG. 33).

Close evaluation of the kinetic data reveals that the turnover frequency (TOF), i.e. mol C$_3$H$_8$ reacted per mol V per s, is reduced by approximately a factor of 1.7 in the case of the V/pro-SiO$_2$, compared to supported vanadia materials on un-promoted SiO$_2$. Assuming a constant pre-exponential factor, this corresponds to a subtle difference in activation energy of ≈0.7 kcal mol$^{-1}$. This decrease in TOF upon sodium promotion could be due to the generation of slightly less-reactive V=O sites, caused by the interaction of the vanadyl oxygen atom with the sodium promoter (vide supra). We emphasize that there is a significant spread in the reported literature for TOF values for V/SiO$_2$ catalysts for ODHP, varying between almost three orders of magnitude (10$^{-4}$-6×10$^{-2}$ s$^{-1}$) [6]. Based on the results shown here, this spread could be due to varying levels of impurities found in the silica and warrants caution when comparing literature data [6]. In any case, this minor decrease in TOF caused by the sodium promoter is more than compensated by a nearly three-fold enhancement of the monolayer coverage, leading to an overall increase in space-time-yield for V/pro-SiO$_2$ materials.

Following our earlier observation that also other Group V metal oxides show enhanced 2D dispersion when supported on Na+-promoted SiO$_2$ [18], we attempted to co-immobilize a second metal oxide, approaching a combined monolayer. As Ta/SiO$_2$ has been reported in the literature as a very active [24], but less selective ODHP catalyst, we focused our attention on the preparation of a V/Ta/SiO$_2$ catalyst (containing 4 wt % V and 18 wt % Ta), featuring a surface coverage of ≈8 (V+Ta) per nm$^2$. Remarkably, this ternary metal oxide catalyst shows a significantly improved catalytic performance over the V/pro-SiO$_2$ material. Indeed, the 4V/18Ta/pro-SiO$_2$ catalyst shows substantially higher selectivity to propylene than all other supported catalysts, maintaining close to 80% propylene selectivity at 5.4% propylene yield (FIG. 33). In addition to improved selectivity, the ternary 4V/18Ta/pro-SiO$_2$ catalyst also becomes more active. The combination of these favorable catalytic properties result in improved productivity for the 4V/18Ta/pro-SiO$_2$ over its V/pro-SiO$_2$ counterparts (FIG. 34). As far as we are aware, this is the first example of a ternary supported metal oxide catalyst for ODHP that results in an enhanced productivity (space-time-yield) and increased selectivity to propylene. The molecular reasons for this enhanced performance are currently not yet clear. Yet, $^{51}$V NMR seems to suggest that the vanadium is bound to the silica and not to the tantalum (FIG. 31). However, the peak broadening and asymmetry, compared to a V/pro-SiO$_2$ with similar vanadium loading, seems to suggest that the tantalum electronically affects the vanadyl species. This effect can also be observed on the vanadyl stretching vibration in Raman (FIG. 29).

Importantly, these results suggest that an optimal amount of a third transition metal oxide at sub-monolayer coverage significantly improves the productivity toward propylene. However, fundamental insights will continue to be explored to explain the increased selectivity and productivity of ternary (VO$_x$)$_m$/(MO$_y$)$_n$/pro-SiO$_2$ type catalysts.

4. Conclusions

Promotion of amorphous silica with small amounts of sodium (pro-SiO$_2$) allows for a greater dispersion of Group V metal oxides. In this contribution we report on Raman and $^{51}$V MAS NMR spectroscopic data, in conjugation with catalytic activity data to further explore this effect. A change in the isotropic $^{51}$V shift from −695 to −675 ppm upon Na$^+$-promotion indicates subtle deshielding of the vanadium center, due to a more positive vanadium site. However, Raman spectroscopy indicates that this does not lead to a stronger V=O bond as one might expect. Indeed, the vanadyl stretch shifts from 1043 to 1038 cm$^{-1}$, indicating that the V=O bond actually weakens. These observations lead to the hypothesis that the Na$^+$ ions weakly interacts with the vanadyl oxygen atom, removing electron density from the V=O bond. This hypothesis is in line with a minor decrease in the turnover frequency (TOF) for the oxidative dehydrogenation of propane reaction (ODHP) for V/pro-SiO$_2$ compared to V/SiO$_2$. Indeed, the rate-determining step in this reaction has been proposed to be the H-abstraction from propane by the vanadyl oxygen atom. Removing electron density from the vanadyl bond would hence lower the reactivity. Nevertheless, the TOF of V/pro-SiO$_2$ still falls well within the range of literature reported TOF of V/SiO$_2$ catalysts for ODHP, which varies by almost three orders of magnitude. This large deviation in reported TOF data might be explained by the potential presence of various impurities for the SiO$_2$ support materials using in the various studies. Successful 2D co-dispersion of both V- and Ta-oxide on pro-SiO$_2$ demonstrates that combinations of supported Group V metal oxides can coexist on the pro-SiO$_2$ surface. This V/Ta/pro-SiO$_2$ ternary catalyst shows improved productivity as well as higher selectivity to propylene for ODHP than 2D V/pro-SiO$_2$ catalysts.

The invention is not limited to the embodiments set forth in this disclosure for illustration, but includes everything that is within the scope of the claims. Furthermore, all documents cited in this disclosure are hereby incorporated by reference in their entirety and for all purposes as if fully set forth in this disclosure.

References in Example 4

1. Rightor E G, Tway C L (2015) Global energy & emissions reduction potential of chemical process improvements. Catal. Today. Doi: http://dx.doi.org/10.1016/j.cattod.2015.02.023
2. The Rising Competitive Advantage of U.S. Plastics (2015) Economics & Statistics Department American Chemistry Council. http://plastics.americanchemistry.com/Education-Resources/PublicationsfThe-Rising-Competitive-Advantage-of-US-Plastics.pdf. Accessed 15 Oct. 2015
3. Trends in Refining (2009) UOP LLC, PedroTech, New Delhi, India. http://energy.wesrch.com/paper-details/pdf-TR1AU1000WZQL-refining-petrochemical-industry-trends#page1. Accessed 15 Oct. 2015
4. Sattler J, Ruiz-Martinez, J, Santillan-Jimenez E, Weckhuysen B M (2014) Chem Rev 114:10613-10653
5. Cavani F, Ballarini N, Cericola A (2007) Catal Today 127:113-131
6. Carrero C A. Schloegl R, Wachs I E, Schomaecker R (2014) ACS Catal 4:3357-3380
7. Schwartz O, Habel D, Otsiter O, Kondratenko E V, Hess C, Schomacker R, Schubert H (2008) J Mol Catal A Chem 293:45-52
8. Carrero C A, Keturakis C, Orrego A, Schomaeker R. Wachs I E (2013) Dalton Trans 42:12644-12653
9. Kondratenko E V, Cherian M, Baerns M (2006) Catal today 112:60-63
10. Kondratenko E V, Cherian M. Baerns M, Su D, Schloegl R, Xiang W, Wachs I E (2005) J Catal 234:131-142
11. Takehira K. Oshishi Y, Shishido T, Kawabata T, Takaki K, Zhang Q, Wang Y (2014) J Catal 224:404-416
12. Shishido T, Shimamura K, Teramura K, Tanaka T (2012) Catal Today 185:151-156
13. Chen K, Bell A T, Iglesia E (2000) J Phys Chem B 104:1292-1299
14. Argyl M D, Chen K, Bell A T, Iglesia E (2002) J Catal 139-149
15. Malleswara R T V, Deo G (2007) AIChE 1538-1549
16. Dinse A, Frank B, Hess C, Habel D, Schomacker R (2008) J Mol Catal A Gen 28-37
17. Carrero C A, Kauer M, Dinse A, Wolfram T, Hamilton N, Trunschke A, Schlogl R, Schomacker R, (2014) Cat Sci Technol 4:786-794
18. Grant J T, Carrero C A, Love A M, Verel R, Hermans I (2015) ACS Catal 5:5787-5793

19. Tian H, Ross E I, Wachs I E (2006) J Phys Chem B 110:9593-9600
20. Gao X, Bare S R, Weckhuysen B M, Wachs I E (1998) J Phys Chem B 102:10842-10852
21. Das N, Eckert H, Hu H, Wachs I E, Walzer J F, Feher F J (1993) J Phys Chem 97:8240-8243
22. McGregor J, pp 195-242 (2009) In: Jackson S D, Hargreaves JSJ *Metal Oxide Catalysis*, Wiley-VCH Verlag GmbH & Co. KGaA Weinheim
23. Hu J Z, Xu S, Li W. Hu M Y, Deng X, Dixon D A, Vasiliu M, Cracium R, Wang Y, Bao X, Peden CHF (2015) ACS Catal 5:3945-3952
24. Jehng J, Tung W, Huang C, Wachs I E (2007) Microporous and Mesoporous Mat 99:299-307

We claim:

1. A heterogeneous catalyst comprising one or more two-dimensional metal oxide species dispersed on the surface of a silica support that further comprises ions of one or more alkali metals wherein the mole ratio of the alkali metal ions present to the metal atoms of the metal oxide present is less than 0.25/1, wherein the metal oxide is aluminum oxide or an oxide of a group 3, group 4, group 5, group 6 or group 7 metal other than molybdenum, and wherein the catalyst is substantially free of metal oxide nanoparticles.

2. The heterogeneous catalyst of claim 1, wherein the one or more two-dimensional metal oxide species are monomeric species.

3. The heterogeneous catalyst of claim 1, wherein the one or more two-dimensional metal oxide species exhibit tetrahedral geometry around the metal atoms.

4. The heterogeneous catalyst of claim 1, wherein the metal oxide is an oxide of a group 5, group 6 or group 7 metal other than molybdenum.

5. The heterogeneous catalyst of claim 4, wherein the metal oxide is an oxide of a group 5 or group 6 metal other than molybdenum.

6. The heterogeneous catalyst of claim 5, wherein the metal oxide is an oxide of a group 5 metal.

7. The heterogeneous catalyst of claim 1, wherein the metal oxide is selected from the group consisting of aluminum oxide, vanadium oxide, niobium oxide, tantalum oxide, chromium oxide, tungsten oxide, rhenium oxide, titanium oxide, and mixtures thereof.

8. The heterogeneous catalyst of claim 7, wherein if vanadium oxide is selected, it is dispersed on the surface of the silica support in the range of 3.2-10 V-atoms/nm$^2$; if niobium oxide is selected, it is dispersed on the surface of the silica support in the range of 1.2-6 Nb-atoms/nm$^2$; and if tantalum oxide is selected, it is dispersed on the surface of the silica support in the range of 1-6 Ta-atoms/nm$^2$.

9. The heterogeneous catalyst of claim 1, wherein the ions of one or more alkalai metals are sodium ions.

10. The heterogeneous catalyst of claim 9, wherein the sodium ions are present in the silica support at a concentration of about 0.15-1.4 Na-ions/nm$^2$.

11. The heterogeneous catalyst of claim 9, wherein the sodium ions are present in the silica support at a concentration of about 0.3-1.0 Na-ions/nm$^2$.

12. The heterogeneous catalyst of claim 9, wherein the sodium ions are present in the silica support at a concentration of about 0.4-0.8 Na-ions/nm$^2$.

13. The heterogeneous catalyst of claim 9, wherein the sodium ions are present in the silica support at a concentration of about 0.6 Na-ions/nm$^2$.

14. A method of making a desired chemical product, comprising contacting a liquid or gaseous reactant with the heterogeneous catalyst of claim 1, whereby the desired chemical product is formed by a process catalyzed by the heterogeneous catalyst.

15. The method of claim 14, wherein the liquid or gaseous reactant is an alkane, the process catalyzed by the heterogeneous catalyst is:
  (a) oxidative dehydrogenation, and the desired chemical product is an olefin;
  (b) non-oxidative dehydrogenation, and the desired chemical product is an olefin; or
  (c) alkane oxidation, and the desired chemical product is an oxygenate.

16. The method of claim 14, wherein the liquid or gaseous reactant comprises one or more olefins, the process catalyzed by the heterogeneous catalyst is olefin metathesis, and the desired chemical product comprises one or more olefins that are different than the olefins of which the liquid or gaseous reactant is comprised.

17. The method of claim 14, wherein the liquid or gaseous reactant is a chlorocarbon, the process catalyzed by the heterogeneous catalyst is chlorocarbon degradation, and the desired chemical product comprise products of chlorocarbon degradation.

18. The method of claim 14, wherein the liquid or gaseous reactant is glycerol, the process catalyzed by the heterogeneous catalyst is glycerol conversion, and the desired chemical product is acrolein.

* * * * *